US005646008A

United States Patent [19]

Thompson et al.

[11] Patent Number: 5,646,008

[45] Date of Patent: Jul. 8, 1997

[54] VERTEBRATE APOPTOSIS GENE: COMPOSITIONS AND METHODS

[75] Inventors: Craig B. Thompson; Lawrence H. Boise, both of Chicago, Ill.; Gabriel Nuñez, Ann Arbor, Mich.

[73] Assignee: The Regent of the University of Michigan, Ann Arbor, Mich.

[21] Appl. No.: 81,448

[22] Filed: Jun. 22, 1993

[51] Int. Cl.[6] ................................ C12N 5/10; C12N 5/12

[52] U.S. Cl. .................. 435/69.1; 435/253.3; 435/320.1; 435/325; 435/358; 435/365; 435/356; 435/367; 435/366; 435/354; 435/369; 435/364; 435/350; 536/23.5; 536/24.31; 536/24.33

[58] Field of Search ................................ 435/320.1, 69.1, 435/240.1, 253.3; 536/23.5, 24.31, 24.33

[56] References Cited

U.S. PATENT DOCUMENTS 5,082,774 1/1992 Heinrich ................................ 435/69.1

OTHER PUBLICATIONS

Allsopp et al., The Proto–Oncogene bcl–2 Can Selectively Rescue Neurotrophic Factor–Dependent Neurons from Apoptosis, *Cell*, 73:295, 1993.

Bakhshi et al., Cloning the Chromosomal Breakpoint of t(14;18) Human Lymphomas: Clustering around $J_H$ on Chromosome 14 and near a Transcriptional Unit on 18, *Cell*, 41:899, 1985.

Borzill et al., Bcl–2 Confers Growth and Survival Advantage to Interleukin 7–dependent Early Pre–B Cells Which Become Factor Independent by a Multistep Process in Culture, *Oncogene*, 7:869, 1992.

Cazals–Hatem et al., Molecular Cloning and DNA Sequence Analysis of cDNA Encoding Chicken Homologue of the Bcl–2 Oncoprotein, *Biochim. Biophys. Acta*, 1132:109, 1992.

Chen–Levy, Z. and Cleary, M.L., Membrane Topology of the Bcl–2 Proto–oncogenic Protein Demonstrated in Vitro, *J. Biol. Chem.*, 265:4929, 1990.

Chen–Levy et al., The bcl–2 Candidate Proto–Oncogene Product Is a 24–Kilodalton Integral–Membrane Protein Highly Expressed in Lymphoid Cell Lines and Lymphomas Carrying the t(14;18) Translocation, *Mol. Cell. Biol.*, 9:701, 1989.

Cleary et al., Cloning and Structural Analysis of cDNAs for bcl–2 and a Hybrid bcl–2/Immunoglobulin Transcript Resulting from the t(14;18) Translation, *Cell*, 47:19, 1986.

Eguchi et al., Isolation and Characterization of the Chicken bcl–2 Gene: Expression in a Variety of Tissues Including Lymphoid and Neuronal Organs in Adult and Embryo, *Nucl. Acids. Res.*, 20:4187, 1992.

Garcia et al., Prevention of Programmed Cell Death of Sympathetic Neurons by the bcl–2 Prot–Oncogene, *Science*, 258:302, 1992.

Graninger et al., Expression of Bcl–2 and Bcl–2–lg Fusion Transcripts in Normal and Neoplastic Cells, *J. Clin. Invest.*, 80:1512, 1987.

Hockenbery et al., Bcl–2 is an Inner Mitochondrial Membrane Protein That Blocks Programmed Cell Death, *Nature*, 348:334, 1990.

Kawabe, Y. and Ochi, A. Programmed Cell Death and Extrathymic Reduction of V$\beta$8$^+$ Cells in Mice Tolerant to *Staphylococcus aureus* Enterotoxin B, *Nature*, 349:245, 1991.

(List continued on next page.)

*Primary Examiner*—Keith C. Furman

*Attorney, Agent, or Firm*—Arnold, White & Durkee

[57] ABSTRACT

The invention relates generally to compositions of and methods for obtaining and using a polypeptide other than BCL-2 that affects programmed vertebrate cell death. The invention relates as well to polynucleotides encoding those polypeptides, recombinant vectors carrying those sequences, the recombinant host cells including either the sequences or vectors, and recombinant polypeptides. The invention further provides methods for using the isolated, recombinant polypeptides in assays designed to select and improve substances capable of altering programmed cell death for use in diagnostic, drug design and therapeutic applications.

12 Claims, 22 Drawing Sheets

```
bcl-x_L                                                    MSQS
bcl-x_S                                                    MSQS

bcl-x_L NRELVVDFLS YKLSQKGYSW SQFSDVEENR TEAPEGTESE METPSAINGN
bcl-x_S NRELVVDFLS YKLSQKGYSW SQFSDVEENR TEAPEGTESE METPSAINGN

bcl-x_L PSWHLADSPA VNGATAHSSS LDAREVIPMA AVKQALREA  GDEFELRYRR
bcl-x_S PSWHLADSPA VNGATAHSSS LDAREVIPMA AVKQALREA  GDEFELRYRR

bcl-x_L AFSDLTSQLH ITPGTAYQSF EQVVNELFRD GVNWGRIVAF FSFGGALCVE
bcl-x_S AFSDLTSQLH ITPGTAYQSF EQ........ .......... ..........
bcl-x_l                         VVNELFRD GVNWGRIVAF FSFGGALCVE

bcl-x_L SVDKEMQVLV SRIAAWMATY LNDHLEPWIQ ENGGWDTFVE LYGNNAAAES
bcl-x_S .......... .......... .......... .....DTFVE LYGNNAAAES
bcl-x_l SVDKEMQVLV SRIAAWMATY LNDHLEPWIQ ENGGW

bcl-x_L RKGQERFNRW FLTGHTVAGV VLLGSLFSRK
bcl-x_S RKGQERFNRW FLTGHTVAGV VLLGSLFSRK
                  *--------------------**
```

OTHER PUBLICATIONS

Korsmeyer, S., Chromosomal Translocations in Lymphoid Malignancies Reveal Novel Proto–Oncogenes, *Annu. Rev. Immunol.*, 10:785–807, 1992.

McCarthy et al., Apoptosis in the development of the immune system: Growth factors, clonal selection and bcl–2, *Cancer Metastasis Reviews*, 11:157–178, 1992.

Nunez et al., Deregulated Bcl–2 Gene Expression Selectively Prolongs Survival of Growth Factor–Deprived Hemopoietic Cell Lines, *J. Immunol.*, 144:3602, 1990.

Raff, M.C., Social controls on cell survival and cell death, *Nature*, 356:397–400, 1992.

Reed et al., Regulation of bcl–2 Proto–Oncogene Expression During Normal Human Lymphocyte Proliferation, *Science*, 236:1295, 1987.

Sentman et al., Bcl–2 Inhibits Multiple Forms of Apoptosis but Not Negative Selection in Thymocytes, *Cell*, 67:879, 1991.

Siegel et al., Inhibition of Thymocyte Apoptosis and Negative and Antigenic Selection in bcl–2 Transgenic Mice, *Proc. Natl. Acad. Sci. USA*, 89:7003, 1992.

Strasser et al., Bcl–2 Transgene Inhibits T Cell Death and Perturba Thymic Self–Censorship, *Cell*, 67:889, 1991.

Strasser et al., Enforced BCL2 Expression in B–lymphoid Cells Prolongs Antibody Responses and Elicits Autoimmune Disease, *Proc. natl. Acad. Sci. USA*, 88:8661, 1991.

Tsujimoto, Y. and Croce, C.M., Analysis of the Structure, Transcripts, and Protein Products bcl–2, the Gene Involved in Human Follicular Lymphoma, *Proc. Natl. Acad. Sci. USA*, 83:5214, 1986.

Vaux et al., Bcl–2 Gene Promotes Haemopoietic Cell Survival and Cooperates with c–myc to Immortalize Pre–B Cells, *Nature*, 335:440, 1988.

Webb et al., Extrathymic Tolerance of Mature T Cells: Clonal Elimination as a Consequence of Immunity, *Cell*, 63:1249, 1990.

Day, R.A. 1983. *How to Write and Publish a Scientific Paper*, iSi Press, Philadelphia, PA, pp. 15–19.

Boise et al. Aug. 1993, Cell 74:597–608.

```
1                                                         ggcgccagcaagctgtcgtgttaaccgt   28

29   ttccttgcctctcttttcctctctgcctgtctgtgcaaaggtcggatgtgttcgccggtcacgagggagcgt   100

101  ggagccaggagctgctaagtgtgctcatctgctcgtgcactggaccatggactcattgagggcgtctcaggt   172

173  gtgaaaatgtccagcagtaaccgggagttagtgattgactttgtttcctacaagctctcgcagaggggcac   244
           MetSerSerSerAsnArgGluLeuValIleAspPheValSerTyrLysLeuSerGlnArgGlyHis

245  tgctggagcgagctggaggaagaggatgagaacaggactgacactgcagctgaggcagagatggacagcgtc   316
     CysTrpSerGluLeuGluGluGluAspGluAsnArgThrAspThrAlaAlaGluAlaGluMetAspSerVal

317  ctcaatgggagcccatcctggcacccccctgccggccacgtagtgaacggagccaccgtgcaccggagcagc   388
     LeuAsnGlySerProSerTrpHisProProAlaGlyHisValValAsnGlyAlaThrValHisArgSerSer

389  ctggaagttcatgaaattgttcgagcatccgacgtgaggcaggcgctgagagatgcgggggatgagtttgag   460
     LeuGluValHisGluIleValArgAlaSerAspValArgGlnAlaLeuArgAspAlaGlyAspGluPheGlu

461  ctgaggtaccggagggctttcagcgacctcacctcccagctccacatcacccctggcacggcgtaccagagc   532
     LeuArgTyrArgArgAlaPheSerAspLeuThrSerGlnLeuHisIleThrProGlyThrAlaTyrGlnSer
```

FIG. 1A-1

```
533  tttgagcaggtagtgaatgaactcttccatgatggtgtgaactggggcgcatcgtggctttcttctccttc   604
     PheGluGlnValValAsnGluLeuPheHisAspGlyValAsnTrpGlyArgIleValAlaPhePheSerPhe
                                       ↓
605  ggaggggctttgtgcgtggagagcgtggacaaggagatgcgggtactggtgggacgcattgtgtcttggatg   676
     GlyGlyAlaLeuCysValGluSerValAspLysGluMetArgValLeuValGlyArgIleValSerTrpMet

677  accacgtacttgaccgaccatctagatccctggatccaggagaatggcggctgggtaagaactgctctccca   748
     ThrThrTyrLeuThrAspHisLeuAspProTrpIleGlnGluAsnGlyGlyTrpValArgThrAlaLeuPro

749  tagggatggctccctgcatcctagctcaaggccagcggcggtgctggccagatcaagcagccttcagtgatt   820

821  gtgcttgtgcttggtctacaccttgcagggcaataaattggtacgtggcccttccctcttcattcttaatgc   892

893  tctgctgcaagagggtcagtccactgtgttgaaacaaagagttaacattctgatttgtcctcctgcatccct   964

965  ttttctcctccttctccctggctgttacataagagacccattttccgagagcctgtggaaatgtaatgtcat  1036

1037 ccaagcttgttcttcaaatgggagcccttgctcttgggcatgttcctcatgtcatttaacagcagggagtgg  1108

1109 agcttcctcccctccgtgctcagcagtgttccagcctggccctgtgatctggtggggtaacagctacttctt  1180

1181 cattctggagatgggacgatgtctgccgctgccatcgcgtggagtgaatcctgcagcagctctctgtgggta  1252

1253 gggctgctgggacgcatcacag/.../ggagcggtgcacccagcgcgcaggaattc
```

FIG. 1A-2

```
                                         .         .         .         .         .
bcl-x      1 ......MSSSNRELVIDFVSYKLSQRGHCWSELEEEDENRTDTAAEAEMD  44
                   : .|||:|:.:: |||||||. |     :.::  ...::.|. .
bcl-2β     1 MAHAGRTGYDNREIVMKYIHYKLSQRGYEW....DAGDVGAAPPGAAPAP  46

                    .         .         .         .         .
bcl-x     45 SVLNGSPSWHPPAGHVVNGATVHRSSLEVHEIVRASD..........VRQ  84
             :::.: |: |.| . . .::..: |.|:... . |..          |:
bcl-2β    47 GIFSSQPG.HTPHPAASRDPVARTSPLQTPAAPGAAAGPALSPVPPVVHL  95

                    .         .         .         .         .
bcl-x     85 ALRDAGDEFELRYRRAFSDLTSQLHITPGTAYQSFEQVVNELFHDGVNWG 134
             |||:|||:|. ||| .|.::.||||:|| || ..|. ||:|||:||||||
bcl-2β    96 ALRQAGDDFSRRYRGDFAEMSSQLHLTPFTARGRFATVVEELFRDGVNWG 145

                    .         .         .         .         .
bcl-x    135 RIVAFFSFGGALCVESVDKEMRVLVGRIVSWMTTYLTDHLDPWIQENGGW 184
             ||||||.|||.:||||||::||..||:.|. |||.||. ||..|||:||||
bcl-2β   146 RIVAFFEFGGVMCVESVNREMSPLVDNIALWMTEYLNRHLHTWIQDNGGW 195

                    .
bcl-x    185 VRTALP.... 190
             | .. .
bcl-2β   196 VGASGDVSLG 205
```

FIG. 1B

```
  1 gaatctctttctctcccttcagaatcttatcttggctttggatcttagaagagaatcactaaccagagacg 71

 72 agactcagtgagtgagcaggtgttttggacaatggactggttgagcccatccctattataaaatgtctcag 143
                                                                    MetSerGln

144 agcaaccgggagctggtggttgactttctctcctacaagctttcccagaaaggatacagctggagtcagttt 215
    SerAsnArgGluLeuValValAspPheLeuSerTyrLysLeuSerGlnLysGlyTyrSerTrpSerGlnPhe

216 agtgatgtggaagagaacaggactgaggccccagaagggactgaatcggagatggagacccccagtgccatc 287
    SerAspValGluGluAsnArgThrGluAlaProGluGlyThrGluSerGluMetGluThrProSerAlaIle

288 aatggcaacccatcctggcacctggcagacagccccgcggtgaatggagccactggccacagcagcagtttg 359
    AsnGlyAsnProSerTrpHisLeuAlaAspSerProAlaValAsnGlyAlaThrGlyHisSerSerSerLeu

360 gatgcccgggaggtgatccccatggcagcagtaaagcaagcgctgagggaggcaggcgacgagtttgaactg 431
    AspAlaArgGluValIleProMetAlaAlaValLysGlnAlaLeuArgGluAlaGlyAspGluPheGluLeu

432 cggtaccggcgggcattcagtgacctgacatcccagctccacatcaccccagggacagcatatcagagcttt 503
    ArgTyrArgArgAlaPheSerAspLeuThrSerGlnLeuHisIleThrProGlyThrAlaTyrGlnSerPhe

504 gaacaggtagtgaatgaactcttccgggatggggtaaactggggtcgcattgtggcctttttctccttcggc 575
    GluGlnValValAsnGluLeuPheArgAspGlyValAsnTrpGlyArgIleValAlaPhePheSerPheGly

576 ggggcactgtgcgtggaaagcgtagacaaggagatgcaggtattggtgagtcggatcgcagcttggatggcc 647
    GlyAlaLeuCysValGluSerValAspLysGluMetGlnValLeuValSerArgIleAlaAlaTrpMetAla
```

FIG. 4A-1

```
648 acttacctgaatgaccacctagagccttggatccaggagaacggcggctgggatactttgtggaactctat 719
    ThrTyrLeuAsnAspHisLeuGluProTrpIleGlnGluAsnGlyGlyTrpAspThrPheValGluLeuTyr

720 gggaacaatgcagcagccgagagccgaaagggccaggaacgcttcaaccgctggttcctgacgggcatgact 791
    GlyAsnAsnAlaAlaAlaGluSerArgLysGlyGlnGluArgPheAsnArgTrpPheLeuThrGlyMetThr

792 gtggccggcgtggttctgctgggctcactcttcagtcggaaatgaccagacactgaccatccactctaccct 863
    ValAlaGlyValValLeuLeuGlySerLeuPheSerArgLys

864 cccacccccttctctgctccaccacatcctccgtccagccgccattgccaccaggagaacccg 926
```

FIG. 4A-2

```
  1 gaatctctttctctcccttcagaatcttatcttggctttggatcttagaagagaatcactaaccagagacg  71

 72 agactcagtgagtgagcaggtgttttggacaatggactggttgagcccatccctattataaaatgtctcag 143
                                                                    MetSerGln

144 agcaaccgggagctggtggttgactttctctcctacaagctttcccagaaaggatacagctggagtcagttt 215
    SerAsnArgGluLeuValValAspPheLeuSerTyrLysLeuSerGlnLysGlyTyrSerTrpSerGlnPhe

216 agtgatgtggaagagaacaggactgaggccccagaagggactgaatcggagatggagacccccagtgccatc 287
    SerAspValGluGluAsnArgThrGluAlaProGluGlyThrGluSerGluMetGluThrProSerAlaIle

288 aatggcaacccatcctggcacctggcagacagccccgcggtgaatggagccactggccacagcagcagtttg 359
    AsnGlyAsnProSerTrpHisLeuAlaAspSerProAlaValAsnGlyAlaThrGlyHisSerSerSerLeu

360 gatgcccgggaggtgatccccatggcagcagtaaagcaagcgctgagggaggcaggcgacgagtttgaactg 431
    AspAlaArgGluValIleProMetAlaAlaValLysGlnAlaLeuArgGluAlaGlyAspGluPheGluLeu

432 cggtaccggcgggcattcagtgacctgacatcccagctccacatcaccccagggacagcatatcagagcttt 503
    ArgTyrArgArgAlaPheSerAspLeuThrSerGlnLeuHisIleThrProGlyThrAlaTyrGlnSerPhe

504 gaacaggatactttgtggaactctatgggaacaatgcagcagccgagagccgaaagggccaggaacgcttc 575
    GluGlnAspThrPheValGluLeuTyrGlyAsnAsnAlaAlaAlaGluSerArgLysGlyGlnGluArgPhe
```

FIG. 4B-1

```
576 aaccgctggttcctgacgggcatgactgtggccggcgtggttctgctgggctcactcttcagtcggaaatga 647
    AsnArgTrpPheLeuThrGlyMetThrValAlaGlyValValLeuLeuGlySerLeuPheSerArgLys

648 ccagacactgaccatccactctaccctcccacccccttctctgctccaccacatcctccgtccagccgccat 719

720 tgccaccaggagaacccg 737
```

FIG. 4B-2

```
bcl-xL                                                          MSQS
bcl-xS                                                          MSQS

bcl-xL NRELVVDFLS YKLSQKGYSW SQFSDVEENR TEAPEGTESE METPSAINGN
bcl-xS NRELVVDFLS YKLSQKGYSW SQFSDVEENR TEAPEGTESE METPSAINGN

bcl-xL PSWHLADSPA VNGATAHSSS LDAREVIPMA AVKQALREA  GDEFELRYRR
bcl-xS PSWHLADSPA VNGATAHSSS LDAREVIPMA AVKQALREA  GDEFELRYRR

bcl-xL AFSDLTSQLH ITPGTAYQSF EQVVNELFRD GVNWGRIVAF FSFGGALCVE
bcl-xS AFSDLTSQLH ITPGTAYQSF EQ........ .......... ..........
bcl-x1                         VVNELFRD GVNWGRIVAF FSFGGALCVE

bcl-xL SVDKEMQVLV SRIAAWMATY LNDHLEPWIQ ENGGWDTFVE LYGNNAAAES
bcl-xS .......... .......... .......... .....DTFVE LYGNNAAAES
bcl-x1 SVDKEMQVLV SRIAAWMATY LNDHLEPWIQ ENGGW

bcl-xL RKGQERFNRW FLTGMTVAGV VLLGSLFSRK
bcl-xS RKGQERFNRW FLTGMTVAGV VLLGSLFSRK
                  *-------------------**
```

FIG. 4C

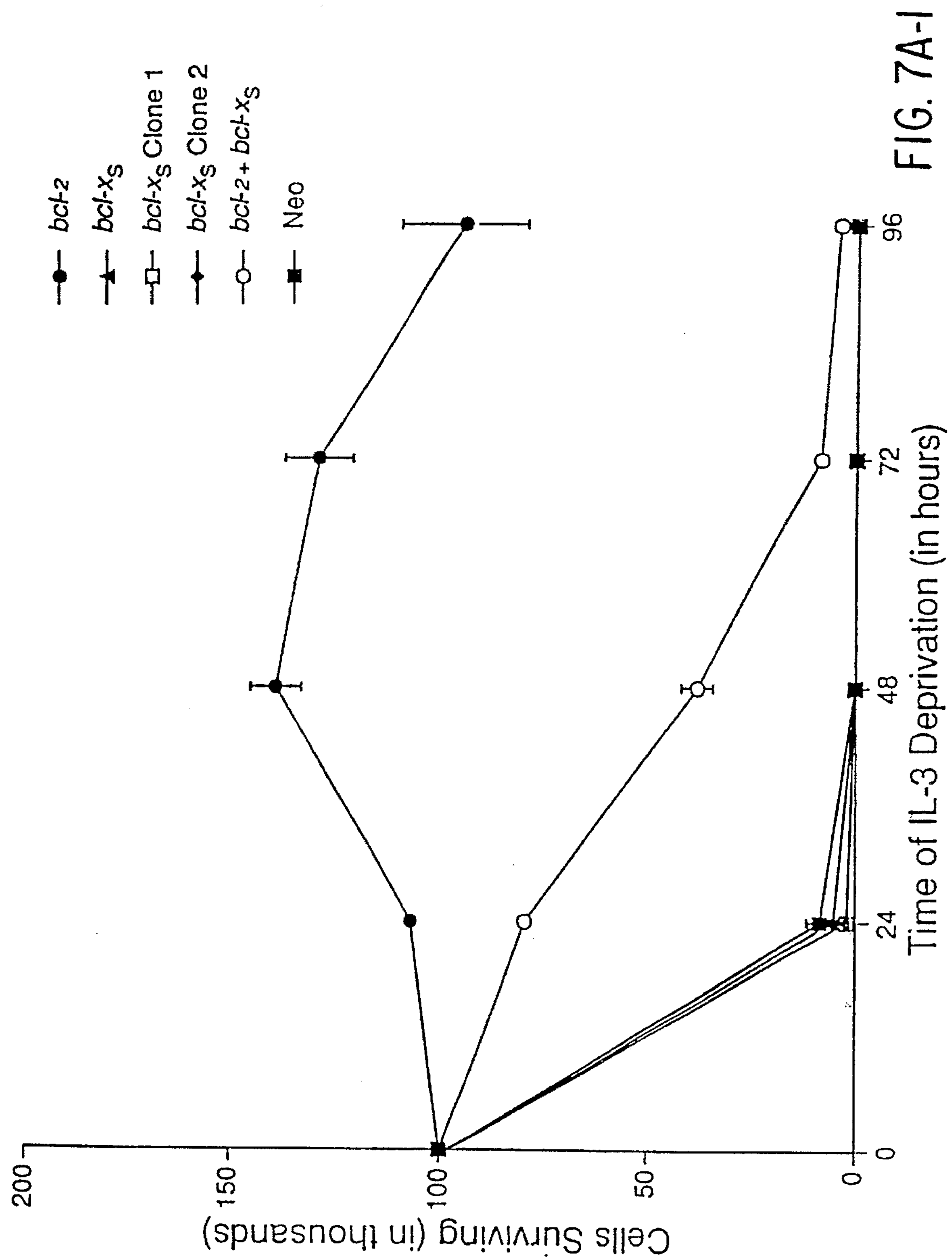
FIG. 7A-I

VERTEBRATE APOPTOSIS GENE: COMPOSITIONS AND METHODS

TECHNICAL FIELD OF THE INVENTION

This invention relates generally to compositions of and methods for altering or regulating programmed vertebrate cell death (apoptosis). The invention relates more particularly to DNA sequences encoding polypeptides that promote or inhibit apoptosis, recombinant vectors carrying those sequences, the recombinant host cells including either the sequences or vectors, and polypeptides. The invention includes as well methods for using the isolated, recombinant polypeptides in assays designed to select and improve among candidate substances that affect apoptosis and polypeptides and polynucleotides for use in diagnostic, drug design and therapeutic applications.

BACKGROUND OF THE INVENTION

The control of cell number in multicellular eukaryotes represents a balance between cell proliferation and cell death. Although a great deal has been learned in recent years about the regulation of cell proliferation, relatively little is known about the regulation of cell death (Ellis et al., 1991; Raff, 1992). Recently, attention has begun to focus on the mechanisms that regulate programmed cell death (apoptosis) (Williams, 1991). Apoptosis is an active process by which many cells die during development and self-maintenance in complex eukaryotes (Kerr et al., 1972). Cell death by apoptosis occurs when a cell activates an internally encoded suicide program as a result of either extrinsic or intrinsic signals. Apoptotic cell death is characterized by plasma membrane blebbing, cell volume loss, nuclear condensation, and endonucleolytic degradation of DNA at nucleosomal intervals (Wyllie et al., 1980).

Two of the best studied vertebrate systems in which programmed cell death plays a role are neural and lymphoid development. During T cell development in the thymus, each individual T cell precursor generates a unique T cell antigen receptor (TCR) by combinatorial rearrangement of TCR gene segments and the cell subsequently undergoes a series of selection processes (Blackman et al., 1990; Rothenberg, 1992). T cells expressing autoreactive TCRs are deleted by apoptosis as a result of negative selection (Murphy et al., 1990). Other cells undergo positive selection through interaction with self-encoded major histocompatibility complex (MHC) molecules expressed on thymic stromal cells, a process which prevents programmed cell death and results in the subsequent MHC-restriction of the mature T cell repertoire. An additional set of thymic cells die as a result of neglect, the absence of either negative or positive selection. Extensive cell death also occurs in the developing nervous system (Cowan et al., 1984; Davies, 1987; Oppenheim, 1991). Following an initial expansion of neurons during development, a significant reshaping of neural structures occurs as a result of the establishment of synaptic interactions. During this reshaping period, the survival of neurons is determined by their supply of neurotrophic growth factors. Cells that become growth-factor deficient die by apoptosis. Once synaptic connections are established, the surviving neurons develop into post-mitotic cells with extended life spans. Thus, programmed cell death plays an essential role in lymphoid development by removing autoreactive T cells and within the nervous system by facilitating the establishment of effective synaptic networks.

Because of the importance of programmed cell death to these developmental processes, considerable interest has arisen in genes that are capable of regulating apoptosis. One of the most important advances in the understanding of the regulation of apoptotic cell death in vertebrates has come from studies of the oncogene bcl-2. bcl-2 was originally cloned from the breakpoint of a t(14;18) translocation present in many human B cell lymphomas (Cleary et al., 1986; Tsujimoto et al., 1986). This translocation results in the deregulated expression of the bcl-2 gene as result of its juxtaposition with the immunoglobulin heavy chain gene locus (Bakhshi et al., 1985). In vitro, BCL-2 ( the gene product of bcl-2) has been shown to prevent apoptotic cell death in cultured cells which are deprived of growth factors (Vaux et al., 1988; Hockenbery et al., 1990; Nuñez et al., 1990; Borzillo et al., 1992; Garcia et al., 1992). However, BCL-2 is not able to block apoptosis in all cells induced by cytokine deprivation or receptor-mediated signalling. For example, BCL-2 prevents apoptosis in hematopoietic cell lines dependent on certain interleukins (IL) IL-3, IL-4, or GM-CSF but it fails to prevent other cell lines from apoptosis following IL-2 or IL-6 deprivation (Nuñez et al., 1990). Overexpression of BCL-2 also fails to prevent antigen receptor-induced apoptosis in some B cell lines (Cuende et al., 1993). In vivo, BCL-2 prevents many, but not all, forms of apoptotic cell death that occur during lymphoid (Sentman et al., 1991; Strasser et al., 1991a; Strasser et al., 1991b; Seigel et al., 1992) and neural (Allsop et al., 1993) development. Expression of a bcl-2 transgene can prevent radiation- and calcium ionophore-induced apoptotic cell death in thymocytes, but does not inhibit the process of negative selection (Sentman et al., 1991; Strasser et al., 1991a). Similarly, overexpression of bcl-2 can prevent apoptosis in neurons dependent on nerve growth factor, but not neurons dependent upon ciliary neurotrophic factor. (Allsop et al., 1993) These results suggest the existence of multiple independent intracellular mechanisms of apoptosis, some of which can be prevented by BCL-2 and others which are unaffected by this gene. Alternatively, these additional pathways may involve proteins that differentially regulate BCL-2 function.

BRIEF SUMMARY OF THE INVENTION

In one aspect, the present invention provides an isolated and purified polynucleotide that encodes a polypeptide other than BCL-2 that promotes or inhibits programmed vertebrate cell death. In a preferred embodiment, a polynucleotide of the present invention is a DNA molecule from a vertebrate species. A preferred vertebrate is a mammal. A preferred mammal is a human. More preferably, a polynucleotide of the present invention encodes polypeptides designated BCL-$X_L$, BCL-$X_S$ and BCL-$X_1$. Even more preferred, a polynucleotide of the present invention encodes a polypeptide comprising the amino acid residue sequence of FIG. 1A(SEQ ID NO:1), FIG. 4A (SEQ ID NO:5), or FIG. 4B (SEQ ID NO:7). Most preferably, an isolated and purified polynucleotide of the invention comprises the nucleotide base sequences of FIG. 1A(SEQ ID NO:1), FIG. 4A (SEQ ID NO:5), or FIG. 4B (SEQ ID NO:7) or their homologues from other vertebrate species.

Yet another aspect of the present invention contemplates an isolated and purified polynucleotide comprising a base sequence that is identical or complementary to a segment of at least 10 contiguous bases of FIG. 1A (SEQ ID NO:1) wherein the polynucleotide hybridizes to a polynucleotide that encodes a polypeptide other than BCL-2 that promotes or inhibits programmed vertebrate cell death. Preferably, the isolated and purified polynucleotide comprises a base sequence that is identical or complementary to a segment of at least 25 to 70 contiguous bases of FIG. 1A (SEQ ID NO:1). For example, a polynucleotide of the invention can comprise a segment of bases identical or complementary to 40 or 55 contiguous bases of the disclosed nucleotide sequences.

In another embodiment, the present invention contemplates an isolated and purified polypeptide other than BCL-2 that promotes or inhibits programmed vertebrate cell death. Preferably, a polypeptide of the invention is a recombinant polypeptide. More preferably, a polypeptide of the present invention is BCL-$X_L$, BCL-$X_S$ and BCL-$X_1$. Even more preferably, a polypeptide of the present invention comprises the amino acid residue sequence of FIG. 1A(SEQ ID NO:2), FIG. 4A (SEQ ID NO:6), or FIG. 4B (SEQ ID NO:8).

In an alternative embodiment, the present invention provides an expression vector comprising a polynucleotide that encodes a polypeptide other than BCL-2 that promotes or inhibits programmed vertebrate cell death. Preferably, an expression vector of the present invention comprises a polynucleotide that encodes BCL-$X_L$, BCL-$X_S$ and BCL-$X_1$. More preferably an expression vector of the present invention comprises a polynucleotide that encodes a polypeptide comprising the amino acid residue sequence of FIG. 1A(SEQ ID NO:2), FIG. 4A (SEQ ID NO:6), or FIG. 4B (SEQ ID NO:8). More preferably, an expression vector of the present invention comprises a polynucleotide comprising the nucleotide base sequence of FIG. 1A(SEQ ID NO:1), FIG. 4A (SEQ ID NO:5), or FIG. 4B (SEQ ID NO:7). Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

In yet another embodiment, the present invention provides a recombinant host cell transfected with a polynucleotide that encodes a polypeptide other than BCL-2 that promotes or inhibits programmed vertebrate cell death. FIG. 1A(SEQ ID NO:1; SEQ ID NO: 2), FIG. 4A (SEQ ID NO:5; SEQ ID NO: 6), and FIG. 4B (SEQ ID NO:7; SEQ ID NO:8) set forth nucleotide and amino acid sequences from the exemplary vertebrates chicken and human. Also contemplated by the present invention are homologous or biologically equivalent polynucleotides and polypeptides other than bcl-2 found in other vertebrates. Preferably, a recombinant host cell of the present invention is transfected with the polynucleotide that encodes BCL-$X_L$, BCL-$X_S$ and BCL-$X_1$. More preferably, a recombinant host cell of the present invention is transfected with the polynucleotide sequence of FIG. 1A(SEQ ID NO:1), FIG. 4A (SEQ ID NO:5), or FIG. 4B (SEQ ID NO:7). Even more preferably, a host cell of the invention is a eukaryotic host cell. Still more preferably, a recombinant host cell of the present invention is a vertebrate cell. Preferably, a recombinant host cell of the invention is a mammalian cell.

In another aspect, a recombinant host cell of the present invention is a prokaryotic host cell. Preferably, a recombinant host cell of the invention is a bacterial cell, preferably a strain of *Escherichia coli*. More preferably, a recombinant host cell comprises a polynucleotide under the transcriptional control of regulatory signals functional in the recombinant host cell, wherein the regulatory signals appropriately control expression of a polypeptide other than BCL-2 that promotes or inhibits programmed vertebrate cell death in a manner to enable all necessary transcriptional and post-transcriptional modification.

In yet another embodiment, the present invention contemplates a process of preparing a polypeptide other than BCL-2 that promotes or inhibits programmed vertebrate cell death comprising transfecting a cell with polynucleotide that encodes a polypeptide other than BCL-2 that promotes or inhibits programmed vertebrate cell death to produce a transformed host cell; and maintaining the transformed host cell under biological conditions sufficient for expression of the polypeptide. Preferably, the transformed host cell is a eukaryotic cell. More preferably still, the eukaryotic cell is a vertebrate cell. Alternatively, the host cell is a prokaryotic cell. More preferably, the prokaryotic cell is a bacterial cell of the DH5α strain of *Escherichia coli*. Even more preferably, a polynucleotide transfected into the transformed cell comprises the nucleotide base sequence of FIG. 1A, FIG. 4A, or FIG. 4B. FIG. 1A (SEQ ID NO:1; SEQ ID NO:2), FIG. 4A (SEQ ID NO:5; SEQ ID NO:6), and FIG. 4B (SEQ ID NO:7; SEQ ID NO:8) set forth nucleotide and amino acid sequences for the exemplary vertebrates chicken and human. Also contemplated by the present invention are homologues or biologically equivalent polynucleotides and polypeptides other than bcl-2 found in other vertebrates.

In still another embodiment, the present invention provides an antibody immunoreactive with a polypeptide other than BCL-2 that promotes or inhibits programmed vertebrate cell death. FIG. 1A (SEQ ID NO:1; SEQ ID NO:2), FIG. 4A (SEQ ID NO:5; SEQ ID NO:6), or FIG. 4B (SEQ ID NO:7; SEQ ID NO:8) set forth nucleotide and amino acid sequences from the exemplary vertebrates chicken and human. Also contemplated by the present invention are antibodies immunoreactive with homologues or biologically equivalent polynucleotides and polypeptides other than bcl-2 found in other vertebrates. Preferably, an antibody of the invention is a monoclonal antibody. More preferably, a polypeptide other than BCL-2 that promotes or inhibits programmed vertebrate cell death is BCL-$X_L$, BCL-$X_S$, or BCL-$X_1$. Even more preferably, a polypeptide comprises the amino acid residue sequence of FIG. 1A(SEQ ID NO:2), FIG. 4A (SEQ ID NO:6), or FIG. 4B (SEQ ID NO:8).

In another aspect, the present invention contemplates a process of producing an antibody immunoreactive with a polypeptide other than BCL-2 that promotes or inhibits programmed vertebrate cell death comprising the steps of (a) transfecting a recombinant host cell with a polynucleotide that encodes a polypeptide other than BCL-2 that promotes or inhibits programmed vertebrate cell death; (b) culturing the host cell under conditions sufficient for expression of the polypeptide; (c) recovering the polypeptide; and (d) preparing the antibody to the polypeptide. FIG. 1A (SEQ ID NO:1; SEQ ID NO:2), FIG. 4A (SEQ ID NO:5; SEQ ID NO:6), and FIG. 4B (SEQ ID NO:7; SEQ ID NO:8) set forth nucleotide and amino acid sequences from the exemplary vertebrates chicken and human. Preferably, the host cell is transfected with the polynucleotide of FIG. 1A(SEQ ID NO:1), FIG. 4A (SEQ ID NO:5), or FIG. 4B (SEQ ID NO:7). Even more preferably, the present invention provides an antibody prepared according to the process described above. Also contemplated by the present invention is the use of homologues or biologically equivalent polynucleotides and polypeptides other than bcl-2 found in other vertebrates to produce antibodies.

Alternatively, the present invention provides a process of detecting a polypeptide other than BCL-2 that promotes or inhibits programmed vertebrate cell death, wherein the process comprises immunoreacting the polypeptide with an antibody prepared according to the process described above to form an antibody-polypeptide conjugate, and detecting the conjugate.

In yet another embodiment, the present invention contemplates a process of detecting a messenger RNA transcript that encodes a polypeptide other than BCL-2 that promotes or inhibits programmed vertebrate cell death, wherein the process comprises (a) hybridizing the messenger RNA transcript with a polynucleotide sequence that encodes that polypeptide to form a duplex; and (b) detecting the duplex. Alternatively, the present invention provides a process of detecting a DNA molecule that encodes a polypeptide other than BCL-2 that promotes or inhibits programmed vertebrate cell death, wherein the process comprises (a) hybridizing DNA molecules with a polynucleotide that encodes a polypeptide other than BCL-2 that promotes or inhibits programmed vertebrate cell death to form a duplex; and (b) detecting the duplex.

In another aspect, the present invention contemplates a diagnostic assay kit for detecting the presence of a polypeptide other than BCL-2 that promotes or inhibits programmed vertebrate cell death in a biological sample, where the kit comprises a first container containing a first antibody capable of immunoreacting with a polypeptide other than BCL-2 that promotes or inhibits programmed vertebrate cell death, with the first antibody present in an amount sufficient to perform at least one assay. Preferably, an assay kit of the invention further comprises a second container containing a second antibody that immunoreacts with the first antibody. More preferably, the antibodies used in an assay kit of the present invention are monoclonal antibodies. Even more preferably, the first antibody is affixed to a solid support. More preferably still, the first and second antibodies comprise an indicator, and, preferably, the indicator is a radioactive label or an enzyme.

In an alternative aspect, the present invention provides a diagnostic assay kit for detecting the presence, in biological samples, of a polynucleotide that encodes a polypeptide other than BCL-2 that promotes or inhibits programmed vertebrate cell death, the kits comprising a first container that contains a second polynucleotide identical or complementary to a segment of at least 10 contiguous nucleotide bases of bcl-$x_L$, bcl-$x_S$, or bcl-$x_1$.

In another embodiment, the present invention contemplates a diagnostic assay kit for detecting the presence, in a biological sample, of an antibody immunoreactive with a polypeptide other than BCL-2 that promotes or inhibits programmed vertebrate cell death, the kit comprising a first container containing a polypeptide other than BCL-2 that promotes or inhibits programmed vertebrate cell death that immunoreacts with the antibody, with the polypeptide present in an amount sufficient to perform at least one assay.

In another aspect, the present invention provides a method of preventing or treating programmed cell death in cells, the method comprising:

(a) preparing a non-pathogenic vector comprising the a polynucleotide that encodes a polypeptide other than BCL-2 that promotes or inhibits programmed vertebrate cell death; and (b) introducing the non-pathogenic vector into cells undergoing or likely to undergo programmed cell death.

In a preferred embodiment, the vector comprises a retrovirus, a vaccinia virus, a picornavirus, a coronavirus, a togavirus, or a rhabdovirus altered in such a way as to render it non-pathogenic.

Preferably, the cell is a neuronal cell and the method further comprises introducing the vector into the cells undergoing or likely to undergo programmed cell death by a process comprising transplanting cells of a multipotent neural cell line into a region of the central nervous system in which said neuronal cells undergoing or likely to undergo programmed cell death are located. Alternatively, the vector is introduced into neuronal cells of an animal by injection of the vector at the site of the peripheral nerve endings of the neuronal cells undergoing or likely to undergo cell death or into neuronal cells in culture likely to undergo or undergoing cell death by incubation of the vector with the neuronal cells.

In another aspect, the present invention provides a method of preventing or treating programmed cell death in neuronal cells, the method comprising:

(a) preparing a polypeptide other than BCL-2 that promotes or inhibits programmed vertebrate cell death;

(b) combining the polypeptide with a physiologically acceptable carrier to form a pharmaceutical composition; and (c) administering the composition to neurons likely to undergo or undergoing programmed cell death.

In yet another aspect, the present invention provides a method of delivering a gene that encodes a polypeptide other than BCL-2 that promotes or inhibits programmed vertebrate cell death for gene therapy, the method comprising:

(a) providing the vector of claim 10;

(b) combining the vector with a physiologically acceptable carrier to form a pharmaceutical composition; and (c) administering said pharmaceutical composition so that the vector will reach the intended cell targets.

In a preferred embodiment, the pharmaceutical composition is introduced by injection into an animal at the site of said cell targets and the cell targets are in the central nervous system and the pharmaceutical composition is introduced by injection into an animal at the site of the peripheral nerve ending which originate from neurons located at the site of said cell targets.

In still yet another aspect, the present invention provides a method of treating tumorogenic diseases, the method comprising:

(a) providing an expression vector according to claim 10;

(b) combining the vector with a physiologically acceptable carrier to form a pharmaceutical composition; and (c) administering the composition to tumor cell targets.

BRIEF DESCRIPTION OF THE DRAWINGS

In the drawings, which form a portion of the specification:

FIG. 1A and FIG. 1B. Nucleotide sequence and predicted open reading frame of chicken bcl-x. A-1 and A-2. The nucleotide sequence of chicken bcl-x represents a composite sequence derived from a cDNA clone and the corresponding genomic clone. The cDNA consisted of a 1.3 kb clone whose 5' end is indicated by the arrow. The 5' end of the sequence has been obtained from a genomic clone and shows the 5' end of a predicted open reading frame as well as 257 additional nucleotides ending with a 5' NarI site. The putative initiation codon conforms poorly to the consensus eukaryotic translation initiation sequence while a consensus eukaryotic initiation sequence appears out-of-frame 32 nucleotides 5' of this site. Both the cDNA and genomic sequences end at a natural EcoRI site. B. The amino acid alignment of the predicted open reading frame from chicken bcl-x (upper sequence) to the open reading frame from the human bcl-2b cDNA sequence (lower sequence). A search of GertBank revealed that bcl-x displayed significant homology with all forms of bcl-2 present in GenBank with highest hornology to the bcl-2b form. Like the bcl-2b cDNA, it appears that the bcl-x cDNA arose from an unspliced RNA since it is colinear with the genomic sequence from which it is derived.

In FIG. 4A-1 through 4A-2 and 4B-1 through 4B-2 are the predicted open reading frames of two distinct human cDNAs (bcl-$x_L$ and bcl-$x_S$, respectively,) with hornology to chicken bcl-x. In FIG. 4C, the 63 amino acid region of human BCL-$X_L$ deleted in human BCL-$X_S$ is denoted by dots. A predicted 19 amino acid hydrophobic domain and flanking charged residues which are present in both BCL-$X_L$, BCL-$X_S$ are indicated by underlining and asterisks respectively. The average hydrophobicity of this domain which is present in both BCL-$X_L$ and BCL-$X_S$, is 1.3 as calculated by the method of Kyte-Doolittle. FIG. 4 contains three panels.

FIG. 7 consists of three panels.

In FIG. 8A, cells stably transfected with either bcl-2 (J) or bcl-2 plus an expression vector containing bcl-$x_S$ cloned in the reverse orientation (bcl-2+bcl-$x_S$rev; H), or neomycin (Neo; B) alone were analyzed for survival following IL-3 withdrawal. In FIG. 8B, 8C and 8D the level of bcl-2 expression in the above 3 cell types is analyzed on a fluorescence-activated cell sorter by staining permeabilized cells with monoclonal antibodies specific for bcl-2 (thick lines) or an irrelevant control antibody (thin lines).

DETAILED DESCRIPTION OF THE INVENTION

I. The Invention

Figure 2:
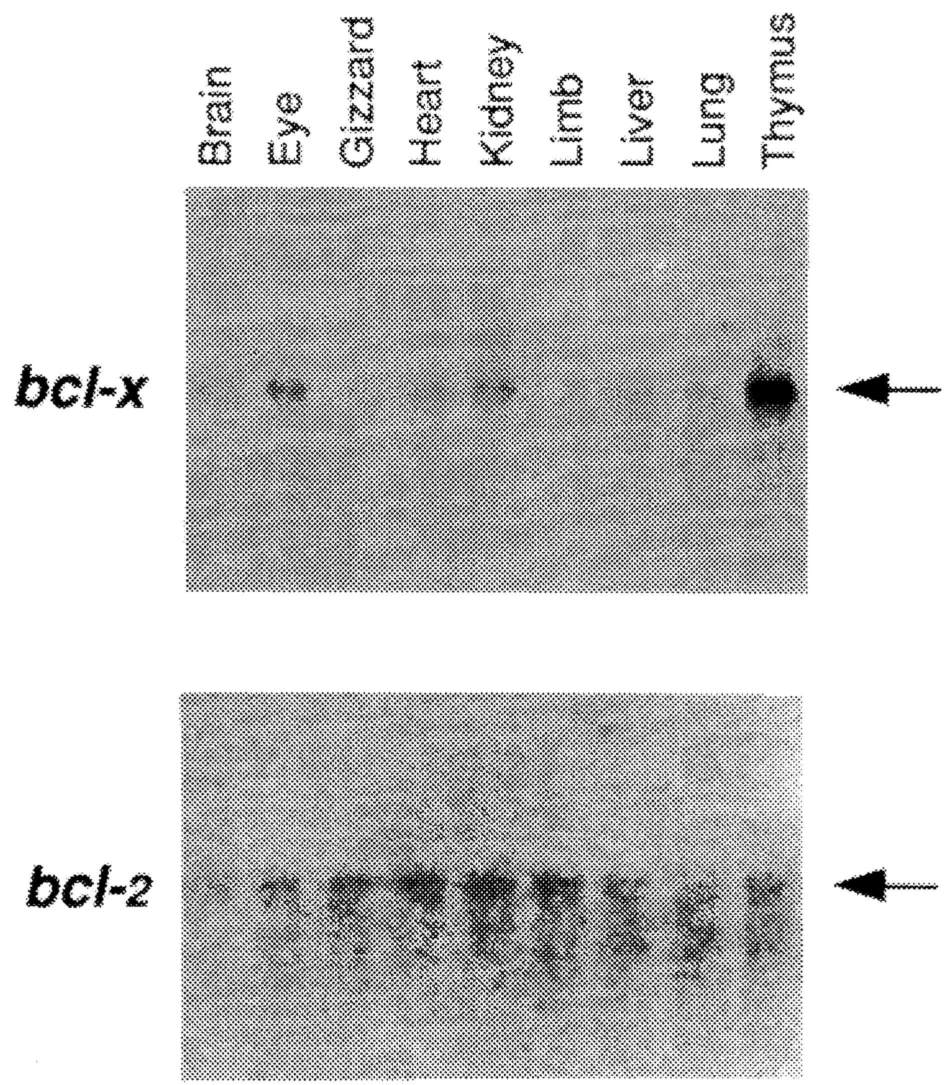
FIG. 2. bcl-x mRNA expression in tissues isolated from a newly hatched chicken. Tissue mRNAs isolated from a chicken on the day of hatching were hybridized with a chicken bcl-x-specific probe as well as a murine bcl-2 probe. While the murine bcl-2 probe recognized a 6.5 kb mRNA indicated by the arrow that was present in all tissues tested, the bcl-x probe hybridized to a 2.7 kb mRNA indicated by the arrow.

The present invention provides DNA segments, purified polypeptides, methods for obtaining antibodies, methods of cloning and using recombinant host cells necessary to obtain and use recombinant apoptosis polypeptides. Accordingly, the present invention concerns generally compositions and methods for the preparation and use of polypeptides other than BCL-2 that promote or inhibit programmed vertebrate cell death.

II. Polynucleotide

A. Isolated and purified polynucleotide that encode polypeptides other than BCL-2 that promote or inhibit programmed vertebrate cell death.

In one aspect, the present invention provides an isolated and purified polynucleotide that encodes a polypeptide other than BCL-2 that promotes or inhibits programmed vertebrate cell death. In a preferred embodiment, a polynucleotide of the present invention is a DNA molecule from a vertebrate species. A preferred vertebrate is a mammal. A preferred mammal is a human. In a preferred embodiment, a polynucleotide of the present invention is a DNA molecule. More preferably, a polynucleotide of the present invention encodes polypeptides designated BCL-$X_1$, BCL-$x_S$ and BCL-$X_1$. Even more preferred, a polynucleotide of the present invention encodes a polypeptide comprising the amino acid residue sequences of FIG. 1A(SEQ ID NO:2), FIG. 4A (SEQ ID NO:6), or FIG. 4B (SEQ ID NO:8). Most preferably, an isolated and purified polynucleotide of the invention comprises the nucleotide base sequences of FIG. 1A(SEQ ID NO:1), FIG. 4A (SEQ ID NO:5), or FIG. 4B (SEQ ID NO:7). In a preferred embodiment, a polynucleotide is bcl-x.

As used herein, the term "polynucleotide" means a sequence of nucleotides connected by phosphodiester linkages. Polynucleotides are presented herein in the direction from the 5' to the 3' direction. A polynucleotide of the present invention can comprise from about 680 to about several hundred thousand base pairs. Preferably, a polynucleotide comprises from about 680 to about 150,000 base pairs. Preferred lengths of particular polynucleotides are set forth hereinafter. As used herein, polynucleotides (e.g., genes) are designated using lower case letters (e.g., bcl-2, bcl-x).

A polynucleotide of the present invention can be a deoxyribonucleic acid (DNA) molecule or ribonucleic acid CRNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U).

A polynucleotide of the present invention can be prepared using standard techniques well known to one of skill in the art. The preparation of a cDNA molecule encoding a polypeptide other than BCL-2 that promotes or inhibits programmed vertebrate cell death of the present invention is described hereinafter in Examples 1 and 3. A polynucleotide can also be prepared from genomic DNA libraries using lambda phage technologies.

In another aspect, the present invention provides an isolated and purified polynucleotide that encodes a polypeptide other than BCL-2 that promotes or inhibits programmed vertebrate cell death, where the polynucleotide is prepamble by a process comprising the steps of constructing a library of cDNA clones from a cell that expresses the polypeptide; screening the library with a labelled cDNA probe prepared from RNA that encodes the polypeptide; and selecting a clone that hybridizes to the probe. Preferably, the polynucleotide of the invention is prepared by the above process. More preferably, the polynucleotide of the invention encodes a polypeptide that has the amino acid residue sequence of FIG. 4A (SEQ ID NO:6) or FIG. 4B (SEQ ID NO:8). More preferably still, the polynucleotide comprises the nucleotide sequence of FIG. 1A (SEQ ID NO:1).

In an initial series of studies we used low stringency hybridization with a murine bcl-2 cDNA probe to identify bcl-2-related genes in chicken lymphoid cells. One of the isolated clones, bcl-x, contained an open reading frame which displayed 44% amino acid identity with human or mouse BCL-2. Southern blotting revealed that chicken BCL-X is encoded by a gene that is distinct from chicken bcl-2. Chicken bcl-x was subsequently used to isolate two distinct cDNAs derived from the human bcl-x gene. These two cDNAs differ in their predicted open reading frames. One cDNA, bcl-$x_L$, contains an open reading frame with 233 amino acids with similar domains to those previously described for bcl-2. The other cDNA, bcl-$x_S$, encodes a 170 amino acid protein in which the region of highest homology to bcl-2 has been deleted. The difference in these two cDNAs arises from differential usage of two 5' splice sites within the first coding exon. When the ability of these two proteins to regulate apoptotic cell death was compared, it was found that BCL-$X_L$ rendered cells resistant to apoptotic cell death upon growth factor deprivation, while BCL-$X_S$ could prevent overexpression of bcl-2 from inducing resistance to apoptotic cell death. Thus, it appears that the regulation of both expression and splicing of bcl-x during development may play a critical role in determining the susceptibility of cells to programmed cell death. Consistent with this hypothesis, we have found that immature thymocytes which are in the process of undergoing selection in the thymus express a high level of bcl-$x_S$ message. The expression of bcl-$x_S$ likely accounts for the inability of bcl-2 to prevent death by negative selection in this cell population. Bcl-$x_S$ can function as a dominant regulator of cell death even in the presence of high level bcl-2 expression. In addition, we have found that mature neural structures constitutively express only the bcl-$x_L$mRNA. Thus, BCL-$X_L$ may contribute to the resistance to programmed cell death and long term viability of this important post-mitotic cell population. Together, our studies suggest that the two bcl-x gene products may regulate one or more BCL-2-independent pathways of apoptotic cell death.

The bcl-x gene has been highly conserved in vertebrate evolution and bcl-x mRNA is expressed in a variety of tissues with the highest levels of mRNA observed in the lymphoid and central nervous systems. We have isolated two distinct bcl-x mRNA species from human tissues. These two cDNAs result from the alternative use of two distinct 5' splice sites located within the first coding exon of the bcl-x gene. The longer cDNA, bcl-$x_L$, encodes a protein that appears to be similar in size and predicted structure to bcl-2. The shorter cDNA, bcl-$x_S$, contains a deletion of the 63 amino acids from the bcl-$x_L$ open reading frame that constitutes the region of highest amino acid identity between BCL-$X_L$ and BCL-$X_S$.

B. Probes and Primers

In another aspect, DNA sequence information provided by the present invention allows for the preparation of relatively short DNA (or RNA) sequences having the ability to specifically hybridize to gene sequences of a selected polynucleotide disclosed herein. In these aspects, nucleic acid probes of an appropriate length are prepared based on a consideration of a selected nucleotide sequences of FIG. 1A(SEQ ID NO:1), FIG. 4A (SEQ ID NO:5), or FIG. 4B (SEQ ID NO:7). Such nucleic acid probes specifically hybridize to a polynucleotide encoding a polypeptide other than BCL-2 that promotes or inhibits programmed vertebrate cell death. Most importantly, the probes can be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a gene or polynucleotide that encodes a polypeptide other than BCL-2 that promotes or inhibits programmed vertebrate cell death from cells using PCR technology.

Figures 4, 7A:
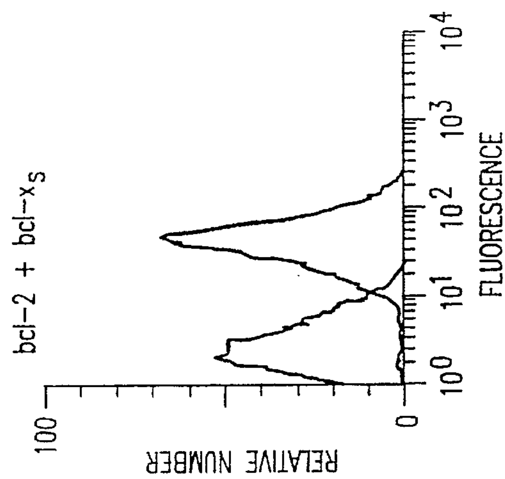
FIG. 4. Predicted amino acid sequence of human mRNAs related to chicken bcl-x.
Figures 3, 7A:
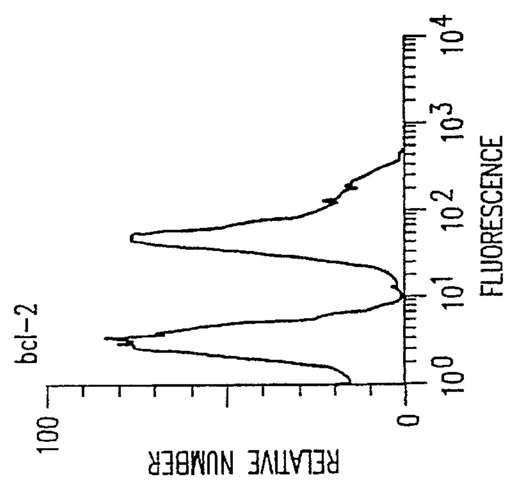
Figures 2, 7A:
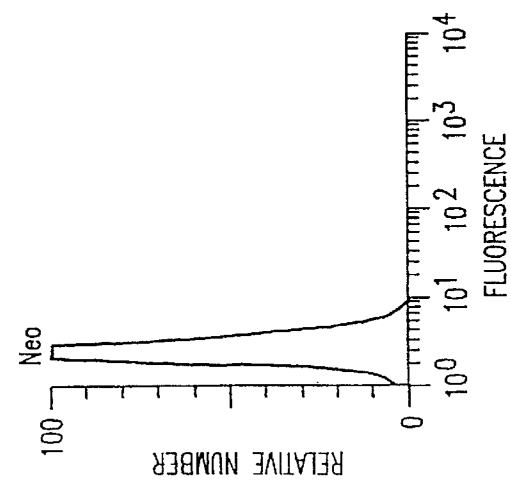

To provide certain of the advantages in accordance with the present invention, a preferred nucleic acid sequence employed for hybridization studies or assays includes probe molecules that are complementary to at least a 10 to 70 or so long nucleotide stretch of a polynucleotide that encodes a polypeptide other than BCL-2 that promotes or inhibits programmed vertebrate cell death, such as that shown in FIG. 1A(SEQ ID NO:1), FIG. 4A (SEQ ID NO:5), or FIG. 4B (SEQ ID NO:7). A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained, one will generally prefer to design nucleic acid molecules having gene-complementary stretches of 25 to 40 nucleotides, 55 to 70 nucleotides, or even longer where desired. Such fragments can be readily prepared by, for example, directly synthesizing the fragment by chemical means, by application of nucleic acid reproduction technology, such as the PCR technology of U.S. Pat. No. 4,603,102, herein incorporated by reference, or by excising selected DNA fragments from recombinant plasmids containing appropriate inserts and suitable restriction enzyme sites.

In another aspect, the present invention contemplates an isolated and purified polynucleotide comprising a base sequence that is identical or complementary to a segment of at least 10 contiguous bases wherein the polynucleotide hybridizes to a polynucleotide that encodes a polypeptide other than BCL-2 that promotes or inhibits programmed vertebrate cell death. Preferably, the isolated and purified polynucleotide comprises a base sequence that is identical or complementary to a segment of at least 25 to 70 contiguous bases of FIG. 1A (SEQ ID NO:1). For example, a polynucleotide of the invention can comprise a segment of bases identical or complementary to 40 or 55 contiguous bases of the disclosed nucleotide sequences.

Accordingly, a polynucleotide probe molecule of the invention can be used for its ability to selectively form duplex molecules with complementary stretches of a gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids. For example, one will select relatively low salt and/or high temperature conditions, such as provided by 0.02M–0.15M NaCl at temperatures of 50° C. to 70° C. Those conditions are particularly selective, and tolerate little, if any, mismatch between the probe and the template or target strand.

Of course, for some applications, for example, where one desires to prepare routants employing a mutant primer strand hybridized to an underlying template or where one seeks to isolate a polypeptide other than BCL-2 that promotes or inhibits programmed vertebrate cell death coding sequence from other cells, functional equivalents, or the like, less stringent hybridization conditions are typically needed to allow formation of the heteroduplex. In these circumstances, one can desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned ihat a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions depend as is well known in the art on the particular circumstances and criteria required (e.g:, on the G+C contents, type of target nucleic acid, source of nucleic acid, size of hybridization probe). Following washing of the matrix to remove nonspecifically bound probe molecules, specific hybridization is detected, or even quantified, by means of the label.

II. Polypeptide other than BCL-2 that promotes or inhibits programmed cell death.

In one embodiment, the present invention contemplates an isolated and purified a polypeptide other than BCL-2 that promotes or inhibits programmed vertebrate cell death. SEQ ID NO:1, SEQ ID NO:2, SEQ ID NO:5, SEQ ID NO:6, SEQ ID NO:7 and SEQ ID NO:8 set forth nucleotide and amino acid sequences from the exemplary vertebrates chicken and human. In a preferred embodiment, a polypeptide of the present invention is a poloypeptide from a vertebrate species. A preferred vertebrate is a mammal. A preferred mammal is a human. Preferably, that polypeptide is a recombinant polypeptide. More preferably, a polypeptide other than BCL-2 that promotes or inhibits programmed vertebrate cell death of the present invention is BCL-$X_L$, BCL-$X_S$ or BCL-$X_1$. Upper case letters (e.g. BCL-X, BLC-2) herein to indicate polypeptides (e.g., products of gene expression). Even more preferably, a polypeptide other than BCL-2 that promotes or inhibits programmed vertebrate cell deaths of the present invention comprises the amino acid residue sequences of SEQ ID NO:2, SEQ ID NO:6 or SEQ ID NO:8.

Polypeptides are disclosed herein as amino acid residue sequences. Those sequences are written left to right in the direction from the amino to the carboxy terminus. In accordance with standard nomenclature, amino acid residue sequences are denominated by either a single letter or a three letter code as indicated below.

| Amino Acid Residue | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Modifications and changes can be made in the structure of a polypeptide of the present invention and still obtain a molecule having like characteristics. For example, certain amino acids can be substituted for other amino acids in a sequence without appreciable loss of receptor activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art (Kyte & Doolittle, *J. Mol. Biol.,* 157: 105–132, 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glummate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glummate (+3.0±1); serine (+0.3); asparagine (+0.2); glummine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glummate and aspartate; serine and threonine; glummine and asparagine; and valine, leucine and isoleucine (See Table 1, below). The present invention thus contemplates functional or biological equivalents of a polypeptide other than BCL-2 that promotes or inhibits programmed vertebrate cell death as set forth above.

TABLE 1

| Original Residue | Exemplary Substitutions |
|---|---|
| Ala | Gly; Ser |
| Arg | Lys |
| Asn | Gln; His |
| Asp | Glu |
| Cys | Ser |
| Gln | Asn |
| Glu | Asp |

TABLE 1-continued

| Original Residue | Exemplary Substitutions |
|---|---|
| Gly | Ala |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |
| Tyr | Trp; Phe |
| Val | Ile; Leu |

Biological or functional equivalents of a polypeptide can also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the underlying DNA. As noted above, such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by *Adelman*, et al. (1983). As will be appreciated, the technique typically employs a phage vector which can exist in both a single stranded and double stranded form. Typical vectors useful in site-directed mutagenesis include vectors such as the M13 phage (*Messing*, et al. 1981). These phage are commercially available and their use is generally known to those of skill in the art.

In general, site-directed mutagenesis in accordance herewith is performed by first obtaining a single-stranded vector which includes within its sequence a DNA sequence which encodes all or a portion of the polypeptide sequence selected. An oligonucleotide primer bearing the desired mutated sequence is prepared, generally synthetically, for example, by the method of *Crea*, et al. (1978). This primer is then annealed to the singled-stranded vector, and extended by the use of enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as *E. coli* cells and clones are selected which include recombinant vectors bearing the mutation. Commercially available kits come with all the reagents necessary, except the oligonucleotide primers.

A polypeptide other than BCL-2 that promotes or inhibits programmed vertebrate cell death of the invention is not limited to a particular source. As disclosed herein, the techniques and compositions of the present invention provide, for example, the identification and isolation of such peptides from animals as diverse as human and chicken. Thus, the invention provides for the general detection and isolation of the genus of polypeptides from a variety of sources while identifying specifically three species of that genus. It is believed that a number of species of the same family of polypeptides are amenable to detection and isolation using the compositions and methods of the present inventions.

A polypeptide of the present invention is prepared by standard techniques well known to those skilled in the art. Such techniques include, but are not limited to, isolation and purification from tissues known to contain that polypeptide, and expression from cloned DNA that encodes such a polypeptide using transformed cells.

Polypeptides that affect or alter programmed vertebrate cell death or apoptosis are found in virtually all mammals including human. Although it is likely that there exist variations between the structure and function of such polypeptides in different species, where such a difference exists, identification of those differences is well within the skill of an artisan in light of the present invention. Thus, the present invention contemplates a polypeptide other than BCL-2 that promotes or inhibits programmed vertebrate cell death from any vertebrate. A preferred mammal is a human. A preferred vertebrate is a mammal.

III. Expression Vectors

In an alternate embodiment, the present invention provide an expression vector comprising a polynucleotide that encodes a polypeptide other than BCL-2 that promotes or inhibits programmed vertebrate cell death. Preferably, an expression vector of the present invention comprises a polynucleotide that encodes polypeptides BCL-$X_L$, BCL-$X_S$ or BCL-$X_1$. In a preferred embodiment, an expression vector of the present invention comprises a polynucleotide that encodes a polypeptide comprising the amino acid residue sequence of SEQ ID NO:2, SEQ ID NO:6 or SEQ ID NO:8. More preferably, an expression vector of the present invention comprises a polynucleotide comprising the nucleotide base sequence of SEQ ID NO:1, SEQ ID NO:5 or SEQ ID NO:7. In a preferred embodiment, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter and further comprises a polyadenylation signal that is positioned 3' of the carboxy-terminal amino acid and within a transcriptional unit of the encoded polypeptide.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (RNA). Transcription-terminating regions are well known in the art. A preferred transcription-terminating region used in an adenovirus vector construct of the present invention comprises a polyadenylation signal of SV40 or the protamine gene.

An expression vector comprises a polynucleotide that encodes a polypeptide other than BCL-2 that promotes or inhibits programmed vertebrate cell death. Such a polypeptide is meant to include a sequence of nucleotide bases encoding a polypeptide other than BCL-2 that promotes or inhibits programmed vertebrate cell death sufficient in length to distinguish said segment from a polynucleotide segment encoding a polypeptide that does not affect programmed vertebrate cell death. A polypeptide of the invention can also encode biologically functional polypeptides or peptides which have variant amino acid sequences, such as with changes selected based on considerations such as the relative hydropathic score of the amino acids being exchanged. These variant sequences are those isolated from natural sources or induced in the sequences disclosed herein using a mutagenic procedure such as site-directed mutagenesis.

Preferably, an expression vector of the present invention comprises a polynucleotide that encodes a polypeptide comprising BCL-$X_L$, BCL-$X_S$, BCL-$X_1$ or the amino acid residue sequence of SEQ ID NO:2, SEQ ID NO:6 or SEQ ID NO:8. An expression vector can include a polypeptide other than BCL-2 that promotes or inhibits programmed vertebrate cell death coding region itself or it can contain coding regions beating selected alterations or modifications in the basic coding region of such a polypeptide other than BCL-2 that promotes or inhibits programmed vertebrate cell death. Alternatively, such vectors or fragments can code larger polypeptides or polypeptides which nevertheless include the basic coding region. In any event, it should be appreciated that due to codon redundancy as well as biological functional equivalence, this aspect of the invention is not limited to the particular DNA molecules corresponding to the polypeptide sequences noted above.

Exemplary vectors include the mammalian expression vectors of the pCMV family including pCMV6b and pCMV6c (Chiron Corp., Emeryville Calif.). In certain cases, and specifically in the case of these individual mammalian expression vectors, the resulting constructs can require co-transfection with a vector containing a selectable marker such as pSV2neo. Via co-transfection into a dihydrofolate reductase-deficient Chinese hamster ovary cell line, such as DG44, clones expressing polypeptides by virtue of DNA incorporated into such expression vectors can be detected.

A DNA molecule of the present invention can be incorporated into a vector, a number of techniques which are well known in the art. For instance, bcl-x, bcl-$x_L$and bcl-$x_S$ were incorporated into pSFFV-Neo and pBluescript-Sk+ using standard techniques (See Examples herinafter).

An expression vector of the present invention is useful both as a means for preparing quantities of the encoding DNA itself, and as a means for preparing the encoded polypeptide. It is contemplated that where a polypeptide of the invention is made by recombinant means, one can employ either prokaryotic or eukaryotic expression vectors as shuttle systems. However, in that prokaryotic systems are usually incapable of correctly processing precursor polypeptides and, in particular, such systems are incapable of correctly processing membrane associated eukaryotic polypeptides, and since eukaryotic polypeptides are anticipated using the teaching of the disclosed invention, one likely expresses such sequences in eukaryotic hosts. However, even where the DNA segment encodes a eukaryotic polypeptide, it is contemplated that prokaryotic expression can have some additional applicability. Therefore, the invention can be used in combination with vectors which can shuttle between the eukaryotic and prokaryotic cells. Such a system is described herein which allows the use of bacterial host cells as well as eukaryotic host cells.

Where expression of recombinant polypeptide of the present invention is desired and a eukaryotic host is contemplated, it is most desirable to employ a vector such as a plasmid, that incorporates a eukaryotic origin of replication. Additionally, for the purposes of expression in eukaryotic systems, one desires to position the polypeptide encoding sequence adjacent to and under the control of an effective eukaryotic promoter such as promoters used in combination with Chinese hamster ovary cells. To bring a coding sequence under control of a promoter, whether it is eukaryotic or prokaryotic, what is generally needed is to position the 5' end of the translation initiation side of the proper translational reading frame of the polypeptide between about 1 and about 50 nucleotides 3' of or downstream with respect to the promoter chosen. Furthermore, where eukaryotic expression is anticipated, one would typically desire to incorporate an appropriate polyadenylation site into the transcriptional unit which includes the desired polypeptide.

The pCMV plasmids are a series of mammalian expression vectors of particular utility in the present invention. The vectors are designed for use in essentially all cultured cells and work extremely well in SV40-transformed simian COS cell lines. The pCMV1, 2, 3, and 5 vectors differ from each other in certain unique restriction sites in the polylinker region of each plasmid. The pCMV4 vector differs from these 4 plasmids in containing a translation enhancer in the sequence prior to the polylinker. While they are not directly derived from the pCMV1-5 series of vectors, the functionally similar pCMV6b and c vectors are available from the Chiron Corp. of Emeryville, Calif. and are identical except for the orientation of the polylinker region which is reversed in one relative to the other.

The universal components of the pCMV plasmids are as follows. The vector backbone is pTZ18R (Pharmacia), and contains a bacteriophage fl origin of replication for production of single stranded DNA and an ampicillin-resistance gene. The CMV region consists of nucleotides −760 to +3 of the powerful promoter-regulatory region of the human cytomegalovirus (Towne stain) major immediate early gene (*Thomsen* et al., 1984,*Boshart* et al., 1985). The human growth hormone fragment (hGH) contains transcription termination and poly-adenylation signals representing sequences 1533 to 2157 of this gene (*Seeburg,* 1982). There is an Alu middle repetitive DNA sequence in this fragment. Finally, the SV40 origin of replication and early region promoter-enhancer derived from the pcD-X plasmid (HindII to PstI fragment) described in (*Okayama* et al., 1983). The promoter in this fragment is oriented such that transcription proceeds away from the CMV/hGH expression cassette.

The pCMV plasmids are distinguishable from each other by differences in the polylinker region and by the presence or absence of the translation enhancer. The starting pCMV 1 plasmid has been progressively modified to render an increasing number of unique restriction sites in the polylinker region. To create pCMV2, one of two EcoRI sites in pCMV1 were destroyed. To create pCMV3, pCMV1 was modified by deleting a short segment from the SV40 region (StuI to EcoRI), and in so doing made unique the PstI, SalI, and BamHI sites in the polylinker. To create pCMV4, a synthetic fragment of DNA corresponding to the 5'-untranslated region of a mRNA transcribed from the CMV promoter was added C. The sequence acts as a translational enhancer by decreasing the requirements for initiation factors in polypeptide synthesis (*Jobling* et al., 1987); *Browning* et al., 1988). To create pCMV5, a segment of DNA (HpaI to EcoRI) was deleted from the SV40 origin region of pCMV1 to render unique all sites in the starting polylinker.

The pCMV vectors have been successfully expressed in simian COS cells, mouse L cells, CHO cells, and HeLa cells. In several side by side comparisons they have yielded 5- to 10-fold higher expression levels in COS cells than SV40-based vectors. The pCMV vectors have been used to express the LDL receptor, nuclear factor 1, Gs alpha polypeptide, polypeptide phosphatase, synaptophysin, synapsin, insulin receptor, influenza hemmagglutinin, androgen receptor, sterol 26-hydroxylase, steroid 17- and 21-hydroxylase, cytochrome P-450 oxidoreductase, beta-adrenergic receptor, folate receptor, cholesterol side chain cleavage enzyme, and a host of other cDNAs. It should be noted that the SV40 promoter in these plasmids can be used to express other genes such as dominant selectable markers. Finally, there is an ATG sequence in the polylinker between the HindIII and PstI sites in pCMU that can cause spurious translation initiation. This codon should be avoided if possible in expression plasmids. A paper describing the construction and use of the parenteral pCMV1 and pCMV4 vectors has been published (Anderson et al., 1989b).

IV. Transfected Cells.

In yet another embodiment, the present invention provides recombinant host cells transformed or transfected with a polynucleotide that encodes a polypeptide other than BCL-2 that inhibits or promotes programmed vertebrate cell death, as well as transgenic cells derived from those transformed or transfected cells. Preferably, a recombinant host cell of the present invention is transfected with a polynucleotide containing sequences from SEQ ID NO:1, SEQ ID NO:5 or SEQ ID NO:7. Means of transforming or transfecting cells with exogenous polynucleotide such as DNA molecules are well known in the art and include techniques such as calcium-phosphate- or DEAE-dextran-mediated transfection, protoplast fusion, electroporation, liposome mediated transfection, direct microinjection and adenovirus infection (*Sambrook, Fritsch and Maniatis,* 1989).

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transported to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandemly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electropotation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. The mechanism of how DNA is delivered into the cell is unclear but transfection efficiencies can be as high as 90%.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

The use of adenovirus as a vector for cell transfection is well known in the art. Adenovirus vector-mediated cell transfection has been reported for various cells (*Stratford-Perricaudet*, et al. 1992).

A transfected cell can be prokaryotic or eukaryotic. Preferably, the host cells of the invention are eukaryotic host cells. A preferred recombinant host cell of the invention is a murine FL5.12 cell. Where it is of interest to produce a human polypeptide other than BCL-2 that promotes or inhibits programmed vertebrate cell deaths, cultured mammalian or human cells are of particular interest.

In another aspect, a recombinant host cell of the present invention is a prokaryotic host cell. Preferably, a recombinant host cell is a bacterial cell of a strain of *Escherichia coli*. In general, prokaryotes are preferred for the initial cloning of DNA sequences and constructing the vectors useful in the invention. For example, *E. coli* K12 strains can be particularly useful. Other microbial strains which can be used include *E. coli* B, and *E. coli* X1776 (ATCC No. 31537). These examples are, of course, intended to be illustrative rather than limiting.

Prokaryotes can also be used for expression. The aforementioned strains, as well as *E. coli* W3110 (F-, lambda-, prototrophic, ATCC No. 273325), bacilli such as *Bacillus subtilus*, or other enterobacteriaceae such as *Salmonella typhimurium* or *Serratus marcesans*, and various Pseudomonas species can be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* can be transformed using pBR322, a plasmid derived from an *E. coli* species (*Bolivar*, et al. 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own polypeptides.

Those promoters most commonly used in recombinant DNA construction include the β-lactamase (penicillinase) and lactose promoter systems (*Chang*, et al. 1978,*Itakura*, et al. 1977; *Goeddel*, et al. 1979; *Goeddel*, et al. 1980) and a tryptophan (TRP) promoter system (EPO Appl. Publ. No. 0036776; Siebwenlist et al., 1980). While these are the most commonly used, other microbial promoters have been discovered and utilized, and details concerning their nucleotide sequences have been published, enabling a skilled worker to introduce functional promoters into plasmid vectors (*Siebwenlist*, et al. 1980).

In addition to prokaryotes, eukaryotic microbes, such as yeast can also be used. *Saccharomyces cerevisiase* or common baker's yeast is the most commonly used among eukaryotic microorganisms, although a number of other strains are commonly available. For expression in Saccharomyces, the plasmid YRp7, for example, is commonly used (*Stinchcomb*, et al. 1979,*Kingsman*, et al. 1979, *Tschemper*, et al. 1980). This plasmid already contains the trpl gene which provides a selection marker for a mutant strain of yeast lacking the ability to grow in tryptophan, for example ATCC No. 44076 or PEP4-1 (*Jones*, 1977). The presence of the trpl lesion as a characteristic of the yeast host cell genome then provides an effective environment for detecting transformation by growth in the absence of tryptophan.

Suitable promoter sequences in yeast vectors include the promoters for 3-phosphoglycerate kinase (Hitzeman, et al. 1980) or other glycolytic enzymes (Hess, et al. 1968; Holland, et al. 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In addition to microorganisms, cultures of cells derived from multicellular organisms can also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (*Kruse and Peterson,* 1973). Examples of such useful host cell lines are AtT-20, VERO and HeLa cells, Chinese hamster ovary (CHO) cell lines, and W138, BHK, COSM6, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

For use in mammalian cells, the control functions on the expression vectors are often derived from viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication (*Fiers*, et al. 1978). Smaller or larger SV40 fragments can also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication can be provided with by construction of the vector to include an exogenous origin, such as can be derived from SV40 or other viral (e.g., Polyoma, Adeno, VSV, BPV, CMV) source, or can be provided by the host cell chromosomal replication mechanism. If the vector is integrated into the host cell chromosome, the latter is often sufficient.

V. Preparing Recombinant Polypeptides Other Than BCL-2 That Affect Programmed vertebrate cell death.

In yet another embodiment, the present invention contemplates a process of preparing a polypeptide other than BCL-2 that affects programmed vertebrate cell death comprising transfecting cells with a polynucleotide that encodes that polypeptide to produce a transformed host cell; and maintaining the transformed host cell under biological conditions sufficient for expression of the polypeptide. Preferably, the transformed host cells is a eukaryotic cell. Alternatively, the host cells is a prokaryotic cell. Preferred prokaryotic cells are bacterial cells of the DH5α strain of *Escherichia coli*. Even more preferably, the polynucleotide transfected into the transformed cells comprises the nucleotide base sequence of SEQ ID NO:1. Most preferably, transfection is accomplished using a hereinbefore disclosed expression vector.

A host cell used in the process is capable of expressing a functional, polypeptide of the present invention. A preferred host cell is a Chinese hamster ovary cell. However, a variety of cells are amenable to a process of the invention, for instance, yeast cells, human cell lines, and other eukaryotic cell lines known well to those of the art.

Following transfection, the cell is maintained under culture conditions for a period of time sufficient for expression of a polypeptide other than BCL-2 that promotes or inhibits programmed vertebrate cell death. Culture conditions are well known in the art and include ionic composition and concentration, temperature, pH and the like. Typically, transfected cells are maintained under culture conditions in a culture medium. Suitable medium for various cell types are well known in the art. In a preferred embodiment, temperature is from about 20° C. to about 50° C., more preferably from about 30° C. to about 40° C. and, even more preferably about 37° C.

pH is preferably from about a value of 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/l and, more preferably from about 290 mosm/L to about 310 mosm/L. Other biological conditions needed for transfection and expression of an encoded protein are well known in the art.

Transfected cells are maintained for a period of time sufficient for expression of a polypeptide other than BCL-2 that promotes or inhibits programmed vertebrate cell death. A suitable time depends inter alia upon the cell type used and is readily determinable by a skilled artisan. Typically, maintenance time is from about 2 to about 14 days.

Recombinant polypeptide is recovered or collected either from the transfected cells or the medium in which those cells are cultured. Recovery comprises isolating and purifying the polypeptide. Isolation and purification techniques for polypeptides are well known in the art and include such procedures as precipitation, filtration, chromatography, electrophoresis and the like.

VI. Antibodies.

In still another embodiment, the present invention provides an antibody immunoreactive with a polypeptide of the present invention. Preferably, an antibody of the invention is a monoclonal antibody. Means for preparing and characterizing antibodies are well known in the art (See, e.g., *Antibodies "A Laboratory Manual*, E. Howell and D. Lane, Cold Spring Harbor Laboratory, 1988).

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogencity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention contemplates a process of producing an antibody immunoreactive with a polypeptide other than BCL-2 that promotes or inhibits programmed vertebrate cell death comprising the steps of (a) transfecting recombinant host cells with a polynucleotide that encodes that polypeptide; (b) culturing the host cells under conditions sufficient for expression of the polypeptide; (c) recovering the polypeptide; and (d) preparing antibodies to the polypeptide. Even more preferably, the present invention provides antibodies prepared according to the process described above.

A monoclonal antibody of the present invention can be readily prepared through use of well-known techniques such as those exemplified in U.S. Pat. No 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supematants for reactivity with an antigen-polypeptides. The selected clones can then be propagated indefinitely to provide the monoclonal antibody.

By way of specific example, to produce an antibody of the present invention, mice are injected intraperitoneally with between about 1–200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and tilering is repeated until a suitable titer is achieved. The spleen of the mouse with the highest titer is removed and the spleen lymphocytes are obtained by homogenizing the spleen with a syringe. Typically, a spleen from an immunized mouse contains approximately $5\times10^7$ to $2\times10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma ceils are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybfidomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

VII. Pharmaceutical Compositions.

In a preferred embodiment, the present invention provides pharmaceutical compositions comprising a polypeptide or polynucleotide of the present invention and a physiologically acceptable carrier. More preferably, a pharmaceutical composition comprises polypeptide BCL-$X_L$, BCL-$X_S$ or BCL-$X_1$ or a polynucleotide that encodes those polypeptides.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer3 s solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A carrier can also be a liposome. Means for using liposomes as delivery vehicles are well known in the art [See, e.g. *Gabizon* et al., 1990; *Ferruti* et al., 1986; and *Ranade, V. V.,* 1989].

A transfected cell can also serve as a carrier. By way of example, a liver cell can be removed from an organism, transfected with a polynucleotide of the present invention using methods set forth above and then the transfected cell returned to the organism (e.g. injected intravascularly).

VIII. Detecting a Polynucleotide or a Polypeptide of the Present Invention.

Alternatively, the present invention provides a process of detecting a polypeptide of the present invention, wherein the process comprises immunoreacting the polypeptides with antibodies prepared according to the process described above to form antibody-polypeptide conjugates, and detecting the conjugates.

In yet another embodiment, the present invention contemplates a process of detecting messenger RNA transcripts that encode a polypeptide of the present invention, wherein the process comprises (a) hybridizing the messenger RNA transcripts with polynucleotide sequences that encode the polypeptide to form duplexes; and (b) detecting the duplex. Alternatively, the present invention provides a process of detecting DNA molecules that encode a polypeptide of the present invention, wherein the process comprises (a) hybridizing DNA molecules with a polynucleotide that encodes that polypeptide to form duplexes; and (b) detecting the duplexes.

IX. Screening Assays

In yet another aspect, the present invention contemplates a process of screening substances for their ability to affect programmed vertebrate cell death comprising the steps of providing a cell that contains a functional polypeptide of the present invention and testing the ability of selected substances to affect programmed vertebrate cell death of that cell.

Utilizing the methods and compositions of the present invention, screening assays for the testing of candidate substances can be derived. A candidate substance is a substance which potentially can promote or inhibit programmed vertebrate cell death, by binding or other intramolecular interaction, with a polypeptide other than BCL-2 that promotes or inhibits programmed vertebrate cell death.

A screening assay of the present invention generally involves determining the ability of a candidate substance to affect the viability of a target cell (susceptibility to programmed vertebrate cell death), such as the screening of candidate substances to identify those that inhibit or promote programmed vertebrate cell death. Target cells can be either naturally occurring cells known to contain a polypeptide of the present invention or transformed cell produced in accordance with a process of transformation set forth hereinbefore.

As is well known in the art, a screening assay provides a cell under conditions suitable for testing programmed vertebrate cell death. These conditions include but are not limited to pH, temperature, tonicity, the presence of relevant factors involved in programmed vertebrate cell death (e.g., growth factor, IL-3), and relevant modifications to the polypeptide such as glycosylation or prenylation. It is contemplated that a polypeptide of the present invention can be expressed and utilized in a prokaryotic or eukaryotic cell. The host cell can also be fractionated into sub-cellular fractions where the receptor can be found. For example, cells expressing the polypeptide can be fractionated into the nuclei, the endoplasmic reticulum, vesicles, or the membrane surfaces of the cell.

pH is preferably from about a value of 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. The presence of factors can be required for the proper testing of programmed vertebrate cell death in specific cells. Such factors include, for example, the presence and absence (withdrawal) of growth factor, interleukins, or colony stimulating factors.

In one embodiment, a screening assay is designed to be capable of discriminating candidate substances having selective ability to interact with one or more of the polypeptides of the present invention but which polypeptides are without a substantially overlapping activity with another of those polypeptides identified herein.

A. Screening assays for a polypeptide of the present invention.

The present invention provides a process of screening a biological sample for the presence of a polypeptide other than BCL-2 that promotes or inhibits programmed vertebrate cell death. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay process, a biological sample is exposed to an antibody immunoreactive with the polypeptide whose presence is being assayed. Typically, exposure is accomplished by forming an admixture in a liquid medium that contains both the antibody and the candidate polypeptide. Either the antibody or the sample with the polypeptide can be affixed to a solid support (e.g., a column or a microtiter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the polypeptide.

Exposure time will vary inter alia with the biological conditions used, the concentration of antibody and polypeptide and the nature of the sample (e.g., fluid or tissue sample). Means for determining exposure time are well known to one of ordinary skill in the art. Typically, where the sample is fluid and the concentration of polypeptide in that sample is about $10^{-10}$M, exposure time is from about 10 minutes to about 200 minutes.

The presence of polypeptide in the sample is detected by detecting the formation and presence of antibody-polypeptide conjugates. Means for detecting such antibody-antigen (e.g., receptor polypeptide) conjugates or complexes are well known in the art and include such procedures as centrifugation, affinity chromatography and the like, binding of a secondary antibody to the antibody-candidate receptor complex.

In one embodiment, detection is accomplished by detecting an indicator affixed to the antibody. Exemplary and well known such indicators include radioactive labels (e.g., $^{32}P$, $^{125}I$, $^{14}C$), a second antibody or an enzyme such as horse radish peroxidase. Means for affixing indicators to antibodies are well known in the art. Commercial kits are available.

B. Screening assay for anti-polypeptide antibody.

In another aspect, the present invention provides a process of screening a biological sample for the presence of antibodies immunoreactive with a polypeptide other than BCL-2 that promotes or inhibits programmed vertebrate cell death (e.g., BCL-$X_L$, BCL-$X_S$or BCL-$X_1$. In accordance with such a process, a biological sample is exposed to a polypeptide other than BCL-2 that promotes or inhibits programmed vertebrate cell death under biological conditions and for a period of time sufficient for antibody-polypeptide conjugate formation and the formed conjugates are detected.

C. Screening assay for polynucleotide that encodes a polypeptide other than BCL-2 that promotes or inhibits programmed vertebrate cell death.

A DNA molecule and, particularly a probe molecule, can be used for hybridizing as an oligonucleotide probe to a DNA source suspected of encoding a polypeptide other than BCL-2 that promotes or inhibits programmed vertebrate cell death. The probing is usually accomplished by hybridizing the oligonucleotide to a DNA source suspected of possessing an apoptosis gene. In some cases, the probes constitute only a single probe, and in others, the probes constitute a collection of probes based on a certain amino acid sequence or sequences of the polypeptide and account in their diversity for the redundancy inherent in the genetic code.

A suitable source of DNA for probing in this manner is capable of expressing a polypeptide of the present invention and can be a genomic library of a cell line of interest. Alternatively, a source of DNA can include total DNA from the cell line of interest. Once the hybridization process of the invention has identified a candidate DNA segment, one confirms that a positive clone has been obtained by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells; (2) means for detecting and isolating other members of the polypeptide family and related polypeptides from a DNA library potentially containing such sequences; (3) primers for hybridizing to related sequences for the purpose of amplifying those sequences; (4) primers for altering native apoptosis DNA sequences; as well as other techniques which rely on the similarity of the DNA sequences to those of the DNA segments herein disclosed.

As set forth above, in certain aspects, DNA sequence information provided by the invention allows for the preparation of relatively short DNA (or RNA) sequences (e.g., probes) that specifically hybridize to encoding sequences of a selected apoptosis gene. In these aspects, nucleic acid probes of an appropriate length are prepared based on a consideration of the encoding sequence for a polypeptide of this invention. The ability of such nucleic acid probes to specifically hybridize to other encoding sequences lend them particular utility in a variety of embodiments. Most importantly, the probes can be used in a variety of assays for detecting the presence of complementary sequences in a given sample. However, uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to at least a 14 to 40 or so long nucleotide stretch of a nucleic acid sequence of the present invention, such as that shown in SEQ ID NO:1. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments can be readily prepared by, for example, directly synthesizing the fragment by chemical means, by application of nucleic acid reproduction technology, such as the PCR technology of U.S. Pat. No. 4,683,202, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M NaCl at temperatures of 50° C. to 70° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate polypeptide coding sequences from related species, functional equivalents, or the like, less stringent hybridization conditions are typically needed to allow formation of the heteroduplex. Under such circumstances, one employs conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

X. Assay kits.

In another aspect, the present invention contemplates diagnostic assay kits for detecting the presence of a polypeptide of the present invention in biological samples, where the kits comprise a first container containing a first antibody capable of immunoreacting with the polypeptide, with the first antibody present in an amount sufficient to perform at least one assay. Preferably, the assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

The present invention also contemplates a diagnostic kit for screening agents. Such a kit can contain a polypeptide of the present invention. The kit can contain reagents for detecting an interaction between an agent and a receptor of the present invention. The provided reagent can be radiolabelled. The kit can contain a known radiolabelled agent capable of binding or interacting with a receptor of the present invention.

In an alternative aspect, the present invention provides diagnostic assay kits for detecting the presence, in biological samples, of a polynucleotide that encodes a polypeptide of the present invention, the kits comprising a first container that contains a second polynucleotide identical or complementary to a segment of at least 10 contiguous nucleotide bases of SEQ ID NO:1.

In another embodiment, the present invention contemplates diagnostic assay kits for detecting the presence, in a biological sample, of antibodies immunoreactive with a polypeptide of the present invention, the kits comprising a first container containing a polypeptide other than BCL-2 that promotes or inhibits programmed vertebrate cell death that immunoreacts with the antibodies, with the polypeptide present in an amount sufficient to perform at least one assay. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media or a microscope slide. When the reagent provided is a dry powder, the powder can be reconstituted by the addition of a suitable solvent. The solvent can be provided.

XI. Treatment of Programmed Cell Death (Apoptosis) with Gene Therapy

In this example, bcl-$x_L$, bcl-$x_S$, or bcl-$x_1$ gene therapy directed toward the prevention or treatment of apoptosis is described. These cells include but are not limited to neuronal cells, cells of the immune system, and cancerous or tumorous cells.

In yet another aspect, the present invention contemplates a process of altering programmed cell death in a cell comprising the steps of:

(a) delivering to the cell an effective amount of a DNA molecule comprising a polynucleotide that encodes a polypeptide other than BCL-2 that inhibits or promotes vertebrate programmed cell death; and (b) maintaining the cell under conditions sufficient for expression of said polypeptide.

In a preferred embodiment, the polypeptide is BCL-$X_L$, BCL-$X_S$ or BCL-$X_1$. Delivery is preferably accomplished by injecting the DNA molecule into the cell. Where the cell is in a subject delivering is preferably administering the DNA molecule into the circulatory system of the subject. In a preferred embodiment, administering comprises the steps of:

(a) providing a vehicle that contains the DNA molecule; and (b) administering the vehicle to the subject.

A vehicle is preferably a cell transformed or transfected with the DNA molecule or a transfected cell derived from such a transformed or transfected cell. An exemplary and preferred transformed or transfected cell is a leukocyte such as a tumor infiltrating lymphocyte or a T cell or a tumor cell from the tumor being treated. Means for transforming or transfecting a cell with a DNA molecule of the present invention are set forth above.

Human lymphocytes can also be transfected with radiation-inducible plasmid constructs using existing technology including retroviral mediated gene transfer (Overell, et al., 1991; Fauser, 1991). In an exemplary embodiment, LAK cells which tend to home in on the tumor site in question with some degree of preference though as is well known, they will also distribute themselves in the body in other locations, may be used to target tumors. Indeed, one of the most important advantages of the radiation inducible system is that only those LAK cells, which are in the radiation field will be activated and will have their exogenously introduced lymphokine genes activated. Thus, for the case of LAK cells, there is no particular need for any further targeting.

Alternatively, the vehicle is a virus or an antibody that specifically infects or immunoreacts with an antigen of the tumor. Retroviruses used to deliver the constructs to the host target tissues generally are viruses in which the 3' LTR (linear transfer region) has been inactivated. That is, these are enhancerless 3'LTR's, often referred to as SIN (self-inactivating viruses) because after productive infection into the host cell, the 3'LTR is transferred to the 5' end and both viral LTR's are inactive with respect to transcriptional activity. A use of these viruses well known to those skilled in the art is to clone genes for which the regulatory elements of the cloned gene are inserted in the space between the two LTR's. An advantage of a viral infection system is that it allows for a very high level of infection into the appropriate recipient cell, e.g., LAK cells.

The viral constructs are delivered into a host by any method that causes the constructs to reach the cells of the target tissue, while preserving the characteristics of the construct used in this invention. By way of example, a rat glioma cell line, C6-BU-1, showed differential susceptibility to herpes simplex virus type 1 (HSV-1) and type 2 (HSV-2), namely, all the HSV-1 strains tested so far persisted in this cell line but the HSV-2 strains did not (Sakihama, et al., 1991). C6-BU-1 cells consist of subpopulations heterogeneous in susceptibility to HSV-1 which may be possibly interchangeable. Furthermore, growth of tumors produced from C6-derived cells bearing the HSV-1 tk gene, but no parental C6 cells, could be inhibited by intraperitoneal administration of ganciclovir (Ezzeddine, et al., 1991). This work demonstrated the effectiveness of the thyroidinc kinase expressed by the HSV-1 tk gene in sensitizing brain tumor cells to the toxic effects of nucleoside analogs. Retrovirus vectors should thus prove useful in the selective delivery of this killer gene to dividing tumor cells in the nervous system, where most endogenous cells are not dividing. Radiation will be used to enhance the specificity of delivery or activation of transcription of the tk gene only in irradiated areas.

Antibodies have been used to target and deliver DNA molecules. An N-terminal modified poly-L-lysine (NPLL)-antibody conjugate readily forms a complex with plasmid DNA (Trubetskoy et al., 1992). A complex of monoclonal antibodies against a cell surface thrombomodulin conjugated with NPLL was used to target a foreign plasmid DNA to an antigen-expressing mouse lung endothelial cell line and mouse lung. Those targeted endothelial cells expressed the product encoded by that foreign DNA.

Target cells for gene therapy can be normal cells or cells not under the proper control of its constitutive genes. For example, many cells die during normal development and self-maintenance. Cancerous or tumorous tissues develop when cells fail to die. Further, neurodegenerative diseases have been implicated with premature neuronal cell death. In addition, premature death of immune system cells have been implicated in autoimmune diseases.

A preferred neuronal cell is any cell of the central nervous system. This neuronal cell type can be a normal neuron or a neuron about to undergo apoptosis. In particular, neuronal cells implicated in neurodegenerative diseases (e.g., such as Parkinson's disease, Amyotrophic Lateral Sclerosis, and Multiple Sclerosis) are contemplated.

A preferrred immune cell is any cell of the immune system, This cell type can be a normal immune system cell or a cell about to undergo apoptosis. It is contemplated that this cell includes but is not limited to B and T lymphocytes, leucocytes and thymocytes.

A preferred cancerous or tumorous cell is any cancerous or tumorous cell. This cell type can be any cell which does not undergo apoptosis. It is contemplated that cancerous cells include but is not limited to cells from prostate cancer, breast cancer, cancers of the immune system, bone cancers, and tumors of the central nervous system.

An expression vector containing bcl-$x_L$, bcl-$x_S$, or bcl-$x_1$ can be introduced into neuoronal cells, cancerous cells, cells of the immune system or other cells in which treatment of apoptosis is desired. One of ordinary skill in the art can choose an appropriate vector for the target cell type.

By way of specific example, mutated HSV-1 virus can be used as a vector for introduction of the gene into neuronal cells. It is also envisioned that this embodiment of the present invention can be practiced using alternative viral or phage vectors, including retroviral vectors and vaccinia viruses whose genome has been manipulated in alternative ways so as to render the virus non-pathogenic. Methods for creating such a viral mutation are set forth in detail in U.S. Pat. No. 4,769,331, incorporated herein by reference. It is also contemplated that multi-potent neural cell lines can be used to deliver the bcl-$x_L$ or bcl-$x_S$ gene to the CNS. These procedures involve taking cells of fetal or postnatal CNS origin, immortalizing and transforming them in vitro and transplanting the cells back into the mouse brain. These cells, after engraftment, follow the migration pattern and environmental cue of normal brain cell development and differentiate in a nontumorigenic, cytoarchitecturally appropriate manner. This work has been examplified in several articles notably Snyder et al., *Cell*, 68: 33–51, 1992 and Ranfranz et al., *Cell*, 66: 713–729, 1991. Utilizing appropriately modified techniques, it is possible to introduce the bcl-$x_L$ or bcl-$x_S$ gene alone or in combination with other genes of interest into the cells and engraft. Such a procedure allows the delivery of the genes to its natural site. Proper expression of the bcl-$x_L$, bcl-$x_S$, or bcl-$x_1$ gene in these neurons should result in prevention of cell death in neurodegeneration and preserving cells carrying foreign genes suitable for gene therapy.

XII. Treatment of Programmed Cell Death (Apoptosis) with a Polypeptide of the Present Invention As an alternative to the gene therapy methods described for exemplary purposes in Examples 2 and 3, neuronal cells undergoing or about to undergo programmed cell death can also be treated with the protein expressed by the bcl-$x_L$, bcl-$x_S$ or bcl-$x_1$ gene, i.e. BCL-$X_L$, BCL-$X_S$ or BCL-$X_1$. Alternatively, a biological functional equivalent protein could be used in such treatment.

For example, BCL-$X_L$, BCL-$X_S$, or BCL-$X_1$ is isolated from cells expressing the protein and purified using conventional chromatography purification and immunoaffinity purification methods described by Ackerman et al. (*J. Virol.* 58: 843–850, 1986, incorporated herein by reference). The purified protein is next combined with a pharmaceutically appropriate carrier, such as buffered saline or purified distilled water. For administration, the pharmaceutical composition can be injected in one of several ways, as appropriate: (i) intraspinal injection; (ii) intraventricular injection; (iii) direct injection into the area containing the neurons undergoing or about to undergo programmed cell death or any other appropriate method of administration understood by those skilled in the art. Such treatment would be particularly appropriate in the surgical repair of severed peripheral nerves, and the use of proteins as therapeutic agents is well within the current level of skill in the medical arts in light of the present specification.

The following examples have been included to illustrate preferred modes of the invention. Certain aspects of the following examples are described in terms of techniques and procedures found or contemplated by the present inventors to work well in the practice of the invention. These examples are exemplified through the use of standard laboratory practices of the inventor. In light of the present disclosure and the general level of skill in the art, those of skill will appreciate that the following examples are intended to be exemplary only and that numerous changes, modifications and alterations can be employed without departing from the spirit and scope of the invention.

EXAMPLE I: Cloning of bcl-x

Avian lymphocytes develop in two distinct organs, the bursa of Fabricius and the thymus. B and T cells developing in these organs share a common feature in that cells from both locations undergo the rapid induction of programmed cell death upon removal from the stromal components of the organ (Cooper et al., 1991; Neiman et al., 1991). We used a murine bcl-2 cDNA probe to clone avian bcl-x. The nucleotide sequence of bcl-x displayed low level sequence identity (56%) with bcl-2, and contained an open reading frame which showed significant similarity to the open reading frame found in the unspliced bcl-2b transcript derived from the bcl-2 gene in both humans and mice (FIG. 1A and FIG. 1B). Sequencing of a genomic fragment containing bcl-x demonstrated that our 1.3 kb cDNA had also arisen from a linear genomic sequence in the absence of splicing. This feature of the sequences raised the possibility that the bcl-x cDNA may have arisen from an unprocessed pseudogene present within the avian genome.

Figure 3:
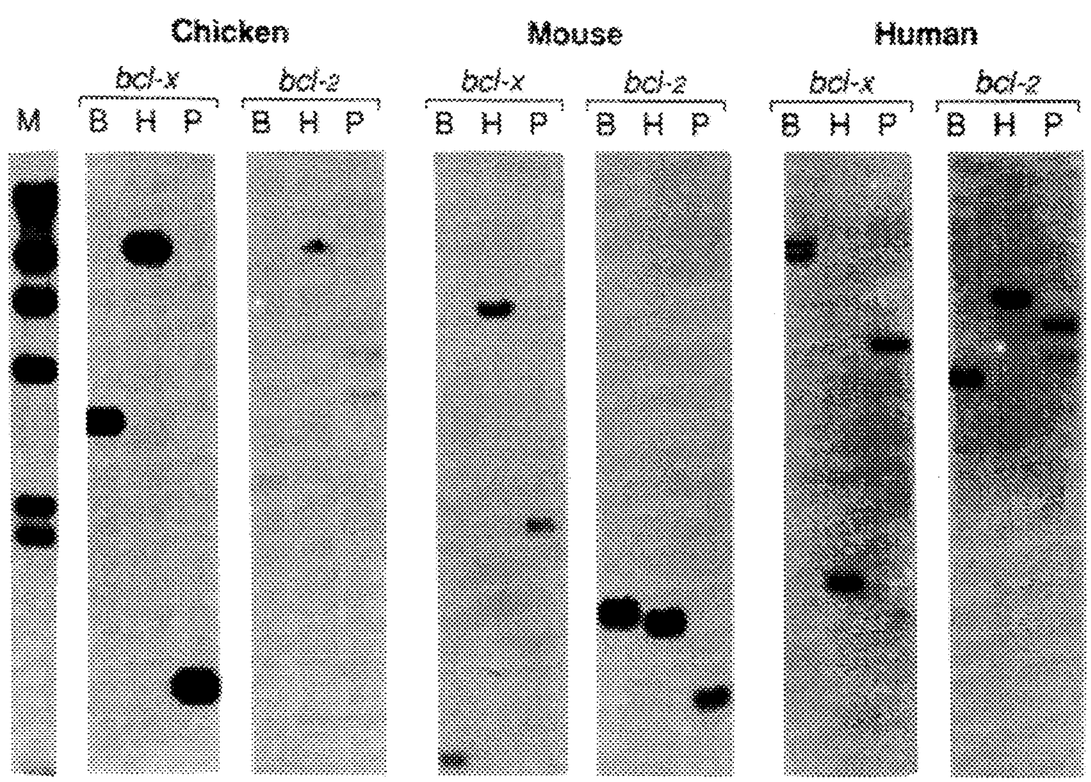
FIG. 3. Southern blot analysis of bcl-x and bcl-2 using chicken, mouse, and human genomic DNA. Genomic DNA from chickens, mice, and humans were digested with BamHI (B), HindIII (H), and PstI (P). The resulting DNA was separated by gel electrophoresis, and then transferred to nitrocellulose. The Southern blots were hybridized with specific probes isolated from the first coding exon of murine bcl-2 and a similar region from chicken bcl-x, and the resulting autoradiograms are shown.

EXAMPLE II: bcl-x Is Expressed in Many Tissues and Is Highly Conserved in Vertebrate Evolution Northern blot analysis of various tissue RNA samples isolated from a newly hatched chicken revealed that a bcl-x specific probe hybridized to a 2.7 kb mRNA species present at highest levels in the thymus and central nervous system (FIG. 2). In contrast a murine bcl-2-specific probe recognized an mRNA species of approximately 6.5 kb present at roughly equal levels in all tissues assayed.

bcl-x is highly condensed in the chicken, mouse and human genomes. Chicken bcl-x and mouse bcl-2 probes hybridized efficiently to DNA from all three species. However, the bcl-x and bcl-2 probes bound to distinct segments of genomic DNA suggesting that they were recognizing independent sequences, both of which have been highly conserved during vertebrate evolution (FIG. 3).

EXAMPLE III: Identification of Two Distinct Human bcl-x cDNAS

We next cloned human homologues of bcl-x. We identified two separate types of human bcl-x cDNAs which contained distinct open reading frames flanked by identical 5' and 3' untranslated sequences. The larger type of cDNA, bcl-$x_L$, contained an open reading frame with greater than 76% nucleotide and 74% amino acid identity (85% amino acid similarity) to chicken bcl-x. However, the human bcl-$x_L$ cDNA diverged from the chicken bcl-x sequence at a position corresponding to where the two coding exons of bcl-2 are joined to form the bcl-2a transcript and where bcl-2a diverges from bcl-2b. It is the bcl-2a transcript that encodes the functional activities previously ascribed to the bcl-2 gene. From the point of its divergence from the chicken bcl-x sequence, the human bcl-$x_L$ open reading frame extends another 45 amino acids before a termination codon is reached. The first 7 out of 8 of these novel amino acids were identical to amino acids encoded by the second coding exon of bcl-2 and present in the bcl-2a but not the bcl-2b mRNAs of both human and mice (FIG. 4A; Tsujimoto et al., 1986; Negrini et al., 1987). The last 36 amino acids encoded by bcl-$x_L$ also showed significant sequence similarity to the hydrophobic domain of bcl-2a thought to play a role in the insertion of the bcl-2 protein into cytoplasmic membranes (Chen-Levy et al., 1989; Chen-Levy and Cleary, 1990). Consistent with the addition of these novel bcl-$x_L$ sequences as a result of mRNA processing, the genomic sequence that encodes the last 45 amino acids of bcl-$x_L$ is found on a separate exon from the exon that encodes the rest of the open reading frame (H. Yang and C. Thompson, unpublished data).

Figure 5:
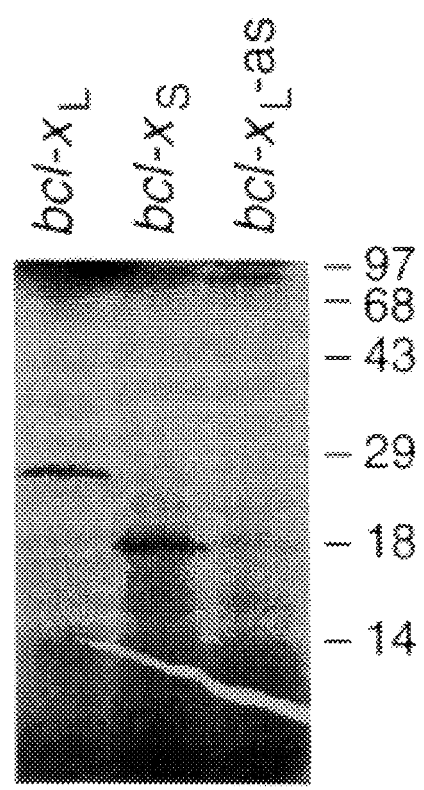
FIG. 5. Translational products of bcl-$x_L$ and bcl-$x_S$ mRNAs. Both bcl-$x_L$ and bcl-$x_S$ mRNAs were subjected to in vitro translation in the presence of 35S-radiolabeled methionine. The resulting translated proteins were run on an SDS-polyacrylamide gel. Sizes of the resulting proteins are indicated on the right in kilodaltons. The result of a translation reaction using bcl-$x_L$ antisense mRNA (bcl-$x_L$-as) is shown as a control to demonstrate the specificity of the translational products.

The second type of human bcl-x-derived cDNA (FIG. 4B) we identified, bcl-$x_S$, differs from bcl-$x_L$ because it lacks the sequence that encodes a stretch of 63 amino acids present within the bcl-$x_L$ open reading frame (this region is indicated as BCL-X1 in FIG. 4C). This deletion occurs as a result of the splicing of the second coding exon observed in bcl-$x_L$ to a more proximal 5' splice donor within the first coding exon. The addition of the 45 amino acids derived from the second coding exon begins precisely at the position of a potential splice donor site, AG/GT, located within the open reading frame of bcl-$x_L$. The use of this splice donor site in forming the bcl-$x_S$ cDNA results in the deletion of the 63 amino acid sequence that displays greatest similarity between bcl-2 and bcl-x. This amino acid sequence encoded for by bcl-x, displays 73% identity with the same region in human bcl-2. This region of bcl-2 is also the most highly conserved region between chicken, murine, and human bcl-2 (Cazals-Hatem et al., 1992; Eguchi et al., 1992).

bcl-$x_L$ and bcl-$x_S$ were transcribed into RNA and then subjected to in vitro translation. As seen in FIG. 5, both bcl-$x_L$ and bcl-$x_S$ cDNAs result in translational products of the approximate size predicted by the open reading frames.

EXAMPLE IV: bcl-$x_L$ Can Serve as an Inhibitor of Apoptotic Cell Death

The murine IL-3-dependent prolymphocytic cell line FL5.12 was transfected with the human bcl-$x_L$ cDNA inserted into the EcoRI cloning site of the pSFFV-Neo expression plasmid. Cells were selected for neomycin resistance for 10 days and then used as a polyclonal population to test their resistance to apoptosis following removal of IL-3. bcl-$x_L$-transfected cells had similar growth kinetics compared to the parental cell line as well as to neomycin-transfected control cells. For comparison, cells were also transfected with the human bcl-2a open reading frame inserted in the EcoRI cloning site of pSFFV-Neo. Neomycin-resistant ceils were then subjected to IL-3 deprivation, and the number of surviving cells was calculated in triplicate beginning at the time of IL-3 deprivation.

Figure 6:
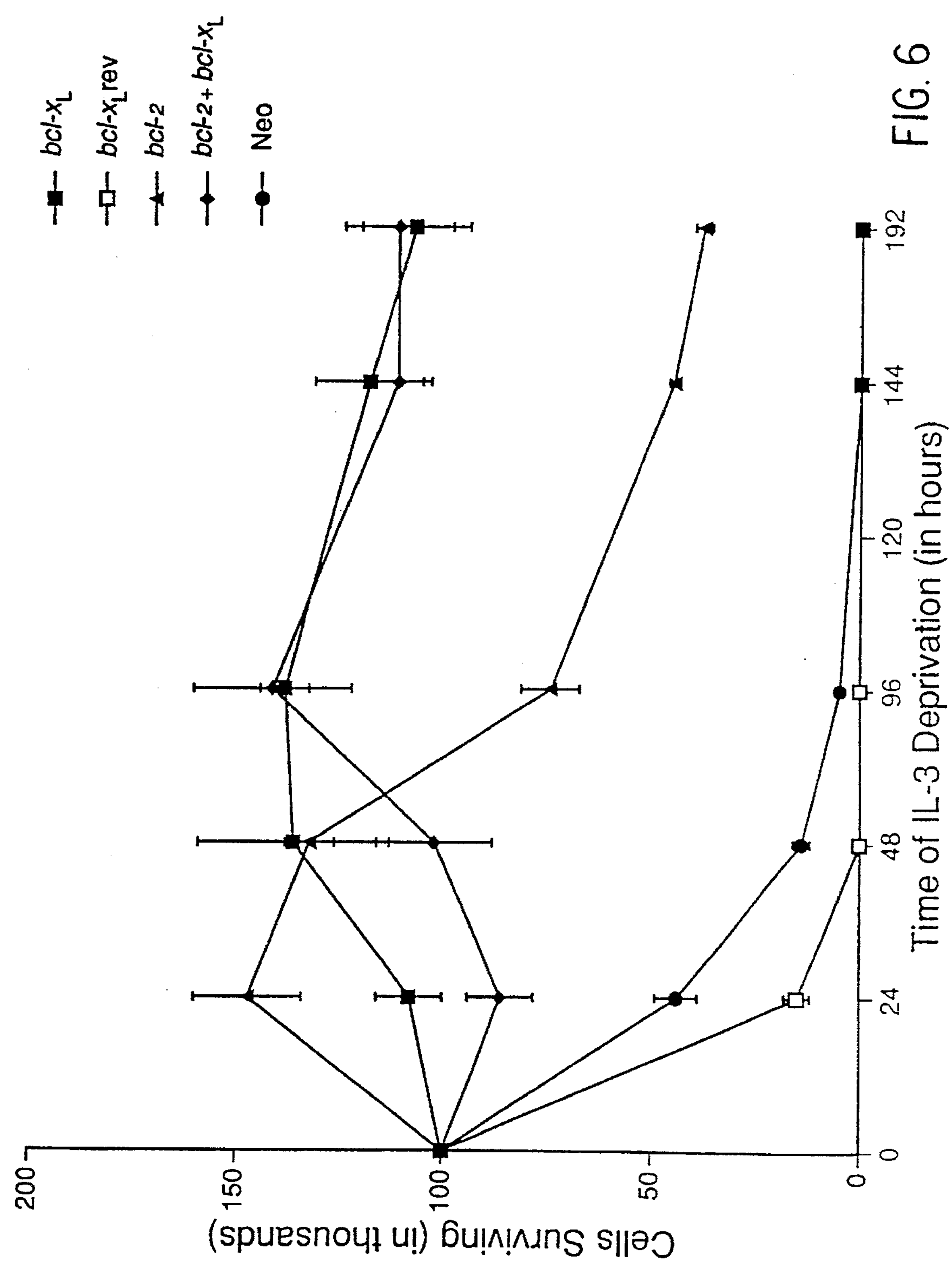
FIG. 6. The effect of bcl-$x_L$ expression on FL5.12 cell survival following IL-3 withdrawal. Stable transfectants of FL5.12 with the pSFFV-Neo vector containing bcl-$x_L$ in the forward (bcl-$x_L$; B) and reverse orientations (bcl-$x_L$-rev; Ñ), bcl-2 (H), bcl-2+bcl-$x_L$ (F), and vector control (Neo; J) were prepared as described in Experimental Procedures. Cell survival was determined by trypan blue exclusion at the indicated time points. Data is presented as the mean +S.D. of triplicate cultures.

As can be seen in FIG. 6, FL5.12 cells transfected with the neomycin construct alone underwent rapid cell death following the removal of the growth factor. Serial examination revealed that these cells underwent apoptosis as manifested by plasma membrane blebbing, cell volume loss, nuclear condensation, and degradation of nuclear DNA at nucleosomal intervals as previously reported (Hockenbery et al., 1990; Nuñez et al., 1990). In contrast, bcl-2-transfected cells demonstrated significant resistance to cell death, and could be readily induced to reenter the cell cycle upon readdition of IL-3. Expression of bcl-2 in greater than 95% of the bulk transfected cells was demonstrated by specific staining with a bcl-2-specific monoclonal antibody.

When stable bcl-$x_L$ transfeetants were subjected to IL-3 deprivation they displayed dramatic resistance to cell death with essentially no loss of cell viability over the 8 day culture period. This resistance to cell death was significantly greater than the resistance of bcl-2-transfected cells in which there was a reproducible 50% decrease in surviving cell number over a similar time period (FIG. 6). Cotransfeetion of bcl-2 and bcl-$x_L$ did not improve cell survival beyond that of transfeetion with bcl-$x_L$ alone. The dramatic survival of bcl-$x_L$-transfeeted cells was not due to ongoing cell proliferation as a result of transformation or the induction of growth factor-independent cell proliferation. Following IL-3 deprivation, the cells rapidly took on a quiescent phenotype arresting in a G0/G1 phase of the cell cycle as measured by cell size and DNA content and did not reenter the cell cycle until IL-3 was readded. Readdition of IL-3 led to rapid blast transformation and cell cycle progression (data not shown). These data suggest that expression of bcl-$x_L$ can lead to significant resistance to apoptotic cell death that is at least as great as that conferred by bcl-2. This property of bcl-$x_L$-transfected cells does not appear to result from cellular transformation that results in IL-3-independent cell growth.

Stable transfection of bcl-$x_L$ prevents apoptotic cell death following growth factor deprivation of an IL-3-dependent cell line to an even greater extent than overexpression of bcl-2. The combination of the two vectors was no better at preventing apoptotic cell death than bcl-$x_L$ alone. This suggests that bcl-$x_L$ plays a major role in regulating the dependence of cells on continuous exogenous signals to prevent cell death.

EXAMPLE V: bcl-xS Can Inhibit the Ability of bcl-2 to Prevent Apoptotic Cell Death.

Figures 1, 7B:
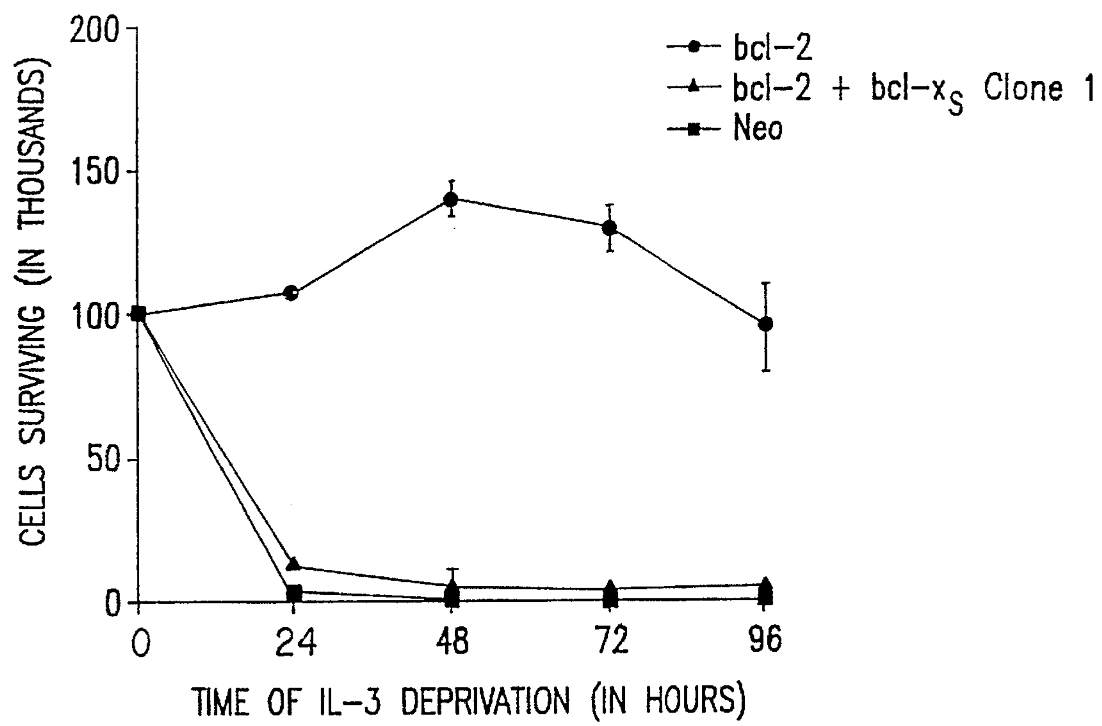
FIG. 1 consists of two panels, FIG 1A and FIG. 1B contains two panels.
Figures 2, 7B:
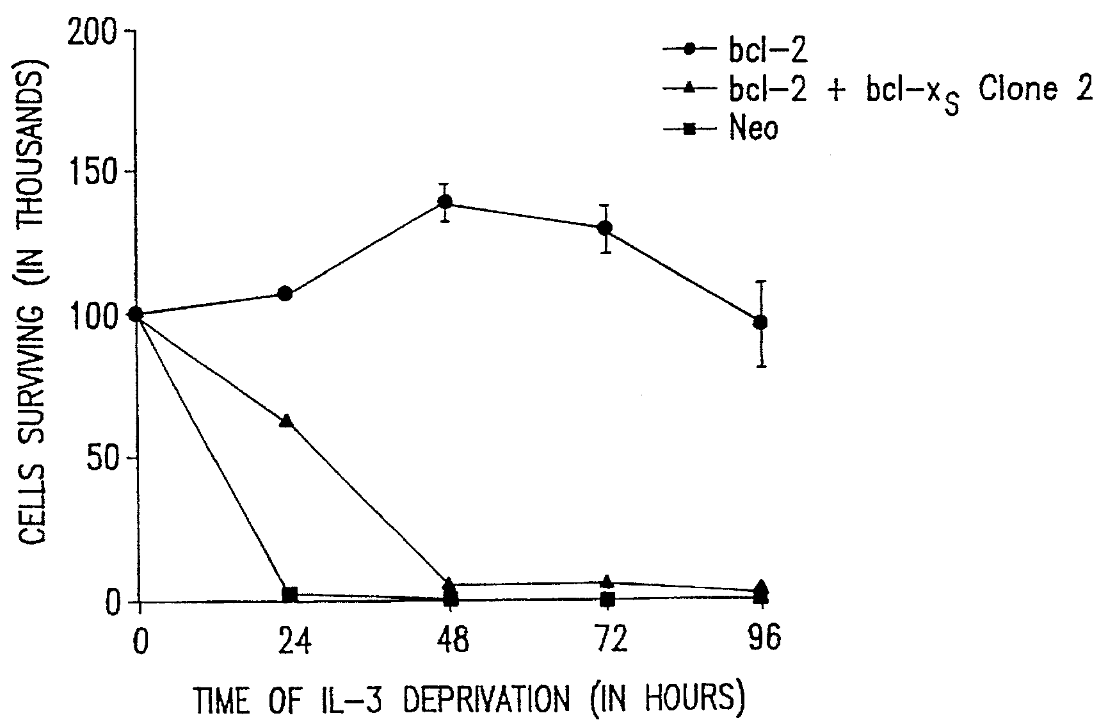
Figures 3, 7B:
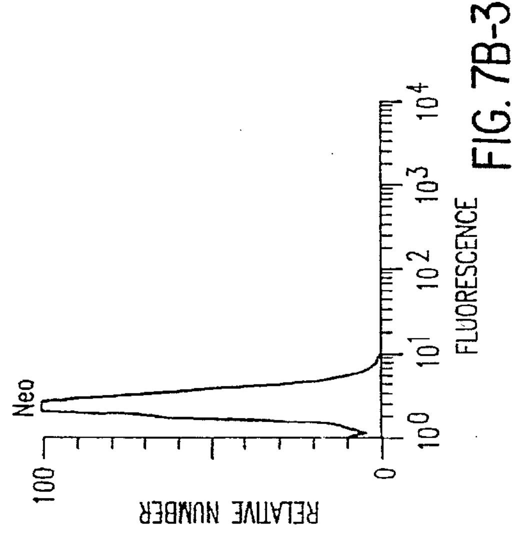
Figures 4, 7B:
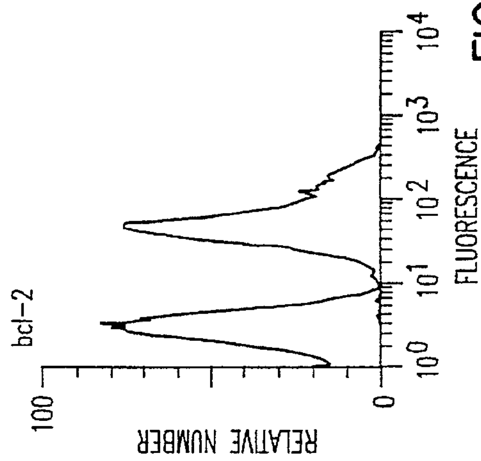
Figures 5, 7B:
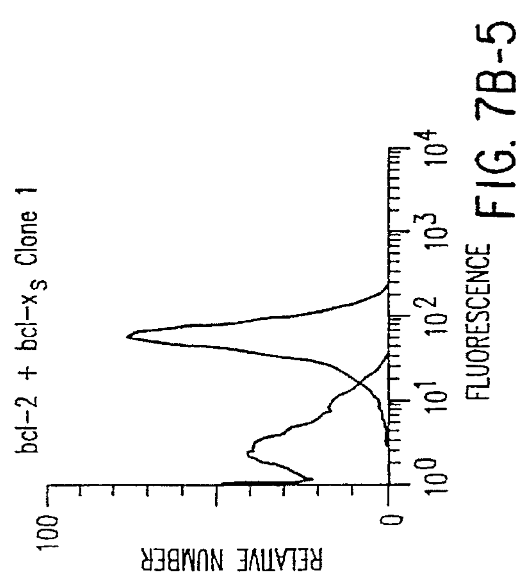
Figures 6, 7B:
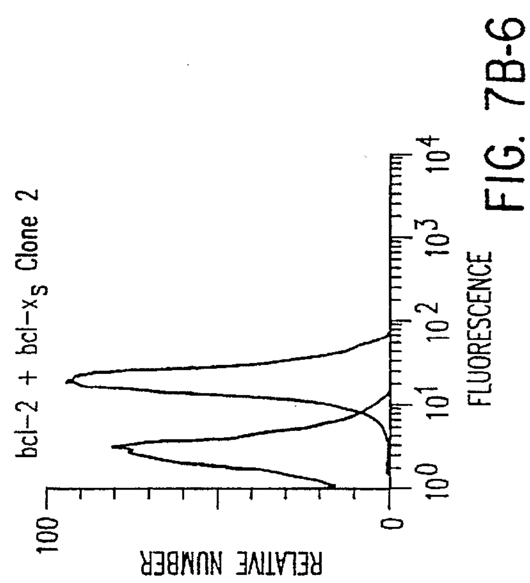
Figure 7C:
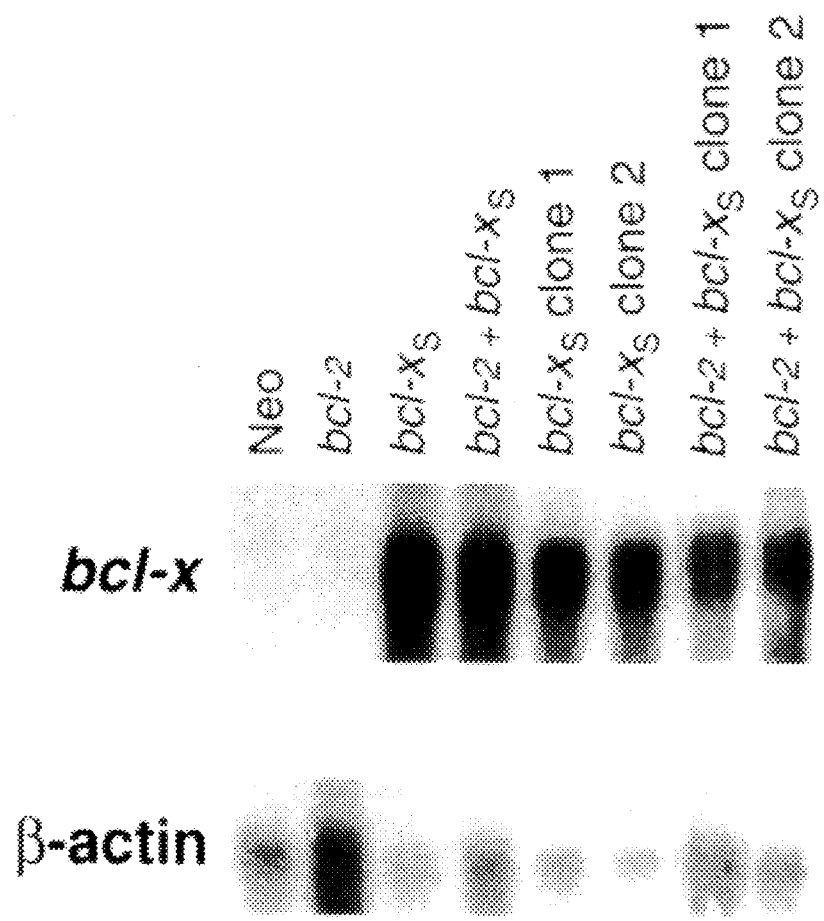
FIG. 7. Stable expression of bcl-xs prevents bcl-2-induced survival of FL.5.12 cells upon IL-3 withdrawal. A-1 through A-4. Stable transfectants of FL5.12 expressing bcl-2 (J), bcl-$x_S$ (H), bcl-2+bcl-$x_S$ (É), or the selectable marker neomycin (Neo; B) alone were prepared as described in Experimental Procedures. In addition, individual subclones of bcl-$x_S$ (bcl-$x_S$ Clone 1 [Ñ] and bcl-$x_S$ Clone 2 [F]) were analyzed. At time zero, exponentially growing cells were withdrawn from IL-3 support, and survival analyzed over time by trypan blue exclusion. The lower portion of the figure shows the flow cytometry analysis of the neomycin (Neo), bcl-2, and bcl-2+bcl-$x_S$ bulk populations. Cells were permeabilized as indicated in the Experimental Procedures, and then stained with a monoclonal antibody specific for human bcl-2 (thick line) or an irrelevant control antibody (thin line). B-1 through B-6. Survival of individual bcl-2+bcl-$x_S$ subclones following IL-3 withdrawal. The survival of subclones expressing both bcl-2 and bcl-$x_S$ were analyzed following growth factor withdrawal as described above (bcl-2+bcl-$x_S$ Clone 1 and bcl-2+bcl-$x_S$ Clone 2). In the lower half of the figure, flow cytometry analysis for bcl-2 expression in the neomycin, bcl-2, bcl-2+bcl-$x_S$ Clone 1, bcl-2+bcl-$x_S$ Clone 2 populations. Cells were permeabilized as described in the Experimental Procedures and then stained with a monoclonal antibody specific for human bcl-2 (thick line) or a irrelevant control isotype-matched antibody (thin line), and the data displayed as fluorescence intensity versus cell number. C. Expression of bcl-x RNA in stably transfected FL5.12 cell lines. RNA was isolated from each of the clones indicated above and analyzed on a Northern blot by hybridization with a bcl-x-specific and b-actin-specific probes.

The bcl-$x_S$ isoform of bcl-x plays a role in the regulation of apoptotic cell death. FL5.12 cells were stably transfected with a human bcl-xS expression plasmid (FIG. 7). Stable transfectants were easily isolated and their expression of bcl-$x_S$ mRNA was confirmed by Northern blot analysis (FIG. 7C). In the presence of IL-3, these cells appeared morphologically normal and displayed growth characteristics indistinguishable from the parental cells or neomycin-transfected controls. Furthermore, the cells died with kinetics indistinguishable from neomycin-transfected control cells upon deprivation of IL-3. bcl-2-transfected cells displayed characteristic resistance to apoptotic cell death upon removal of IL-3. Remarkably, however, when bcl-$x_s$ was cotransfected with bcl-2 and stable transfectants isolated, the cells reacquired sensitivity to growth factor withdrawal, undergoing apoptotic cell death upon IL-3 deprivation. Nevertheless, there was a significant delay in the onset of cell death within this polyclonal population. The sensitivity to IL-3 deprivation of cells co-transfected with bcl-2 and bcl-$x_S$ was not the result of reduced bcl-2 expression since both bulk populations of bcl-2 and bcl-2+bcl-$x_S$ transfected cells displayed roughly equivalent levels of bcl-2 protein. The magnitude of the ability of bcl-$x_S$ to inhibit bcl-2 function, in number of subclones isolated from the co-transfected population of cells was studied. All of these cells expressed high levels of transfected bcl-2, and all demonstrated a reduced resistance to apoptotic cell death upon growth factor withdrawal with some clones demonstrating an almost complete abrogation of bcl-2 function in the presence of bcl-$x_S$ expression (FIG. 7*b*). Furthermore, when assayed at 24 and 48 hours after IL-3 deprivation, DNA from cells co-transfected with bcl-2 and bcl-$x_S$ showed a clear nucleosomal pattern of degradation while DNA from cells transfected with bcl-2 alone or bcl-$x_L$ alone did not (dam not shown). Although there was a correlation between the inhibition of bcl-2 function and the bcl-$x_S$ mRNA levels expressed by the cells, the precise stoichiometry between bcl-$x_S$ expression and bcl-2 functional inhibition was not determined. In subclones which co-express both bcl-2 and bcl-$x_S$, there is significant inhibition of bcl-2-induced resistance to apoptosis by co-expression of bcl-$x_S$. The average survival of bcl-2-transfected cells 96 hours after IL-3 removal was 79+14% (mean +1 S. D., n=3) while the average survival of subclones coexpressing bcl-2 and bcl-$x_S$ was 8+8% (mean +1 S. D., n=6).

Figure 8A:
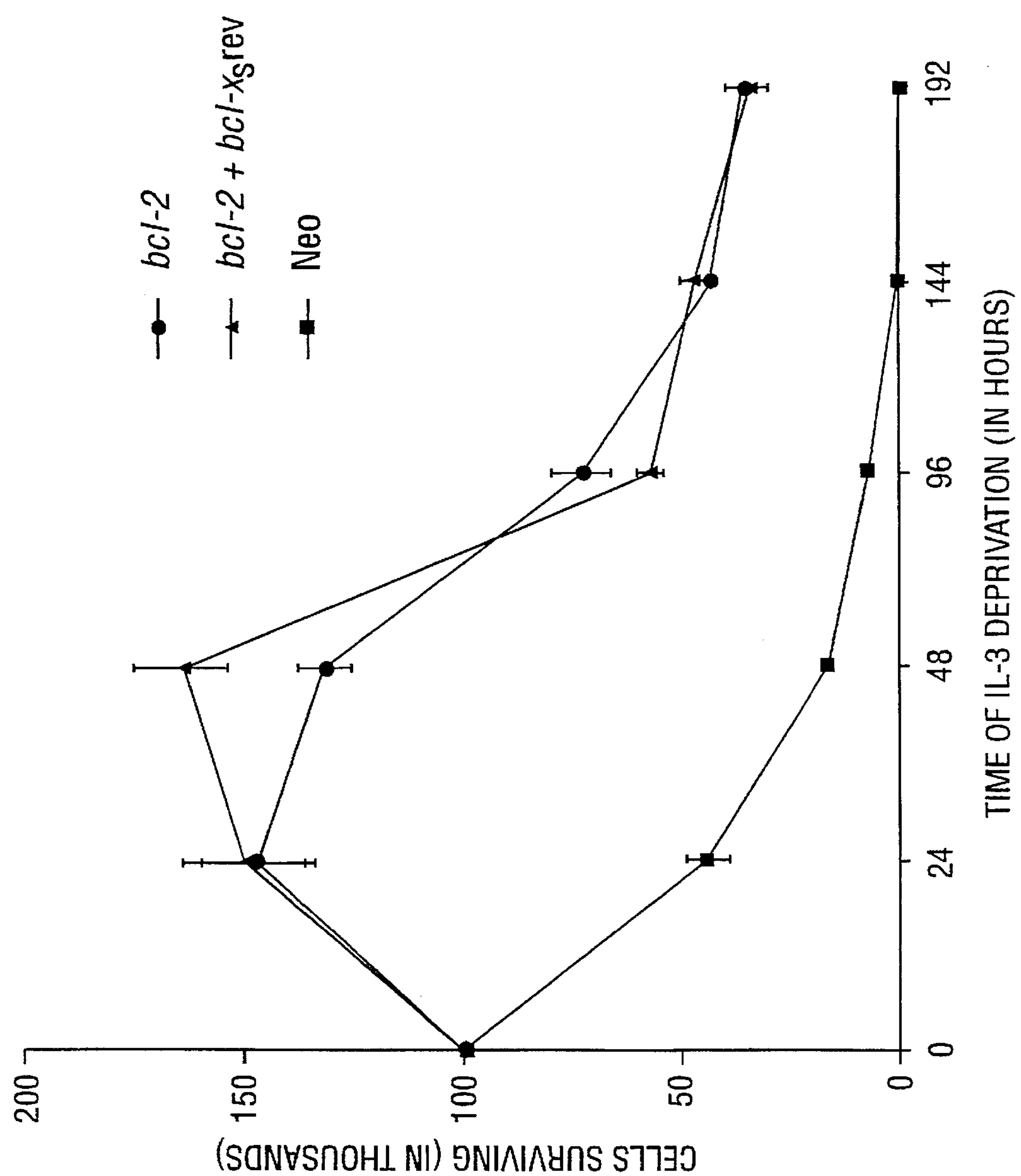
FIG. 8A, 8B, 8C and 8D. bcl-2-induced survival of FL5.12 cells following IL-3 withdrawal is unaffected by antisense bcl-$x_S$ expression.
Figures 8B, 8C, 8D:
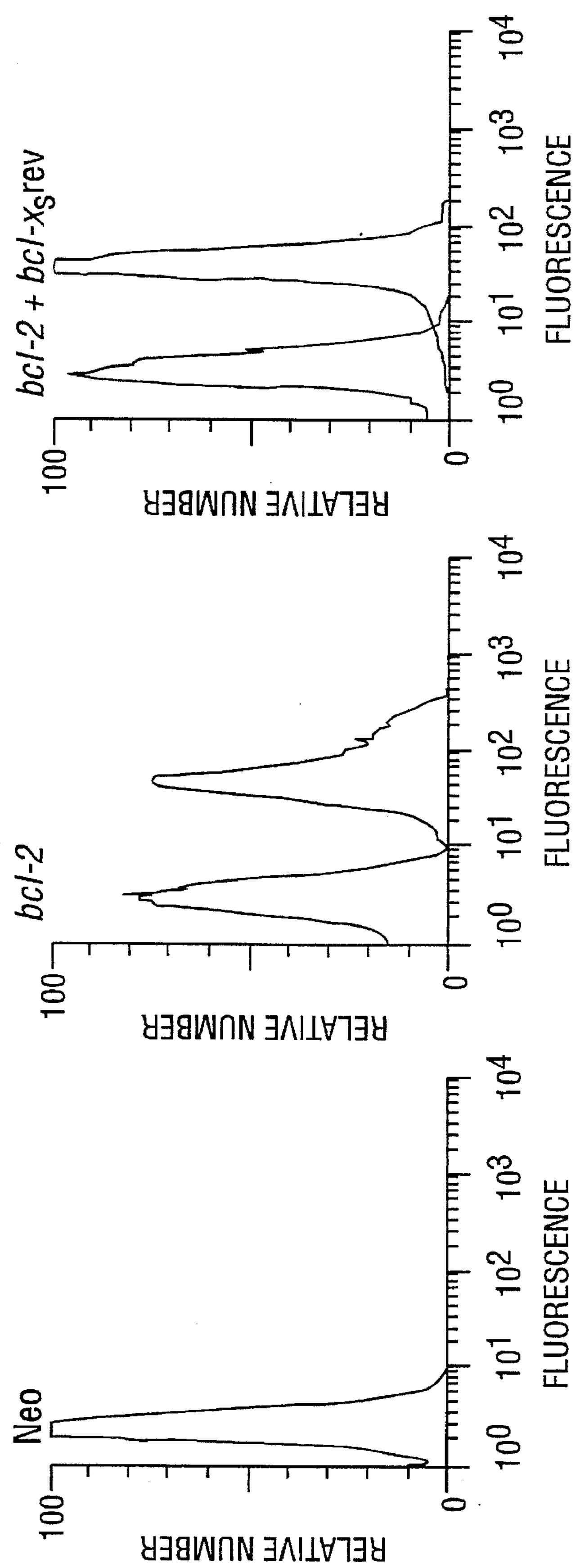

This induction of apoptotic cell death required that the bcl-$x_S$ construct be expressed in the sense orientation, as stable introduction of a pSFFV-Neo plasmid containing bcl-$x_s$ cloned in the antisense orientation had no effect on the ability of bcl-2 to prevent apoptotic cell death upon growth factor deprivation (FIG. 8). The stable expression of bcl-$x_S$ had no effect on cell growth in the presence of growth factor or on the rate of apoptotic cell death following growth factor removal. However, bcl-$x_S$ could prevent the ability of stable bcl-2 expression to inhibit apoptotic cell death upon growth factor removal.

These data suggest that the expression of the bcl-$x_s$ isoform of the bcl-x gene likely plays a dominant role in regulating the ability of other growth survival genes such as bcl-2 to prevent apoptotic cell death.

bcl-$x_S$ expression increased the dependence of the cells on exogenous signals such as growth factors to actively prevent cell death.

EXAMPLE VI: Expression of bcl-x During T Cell Development and Activation.

Figure 9:
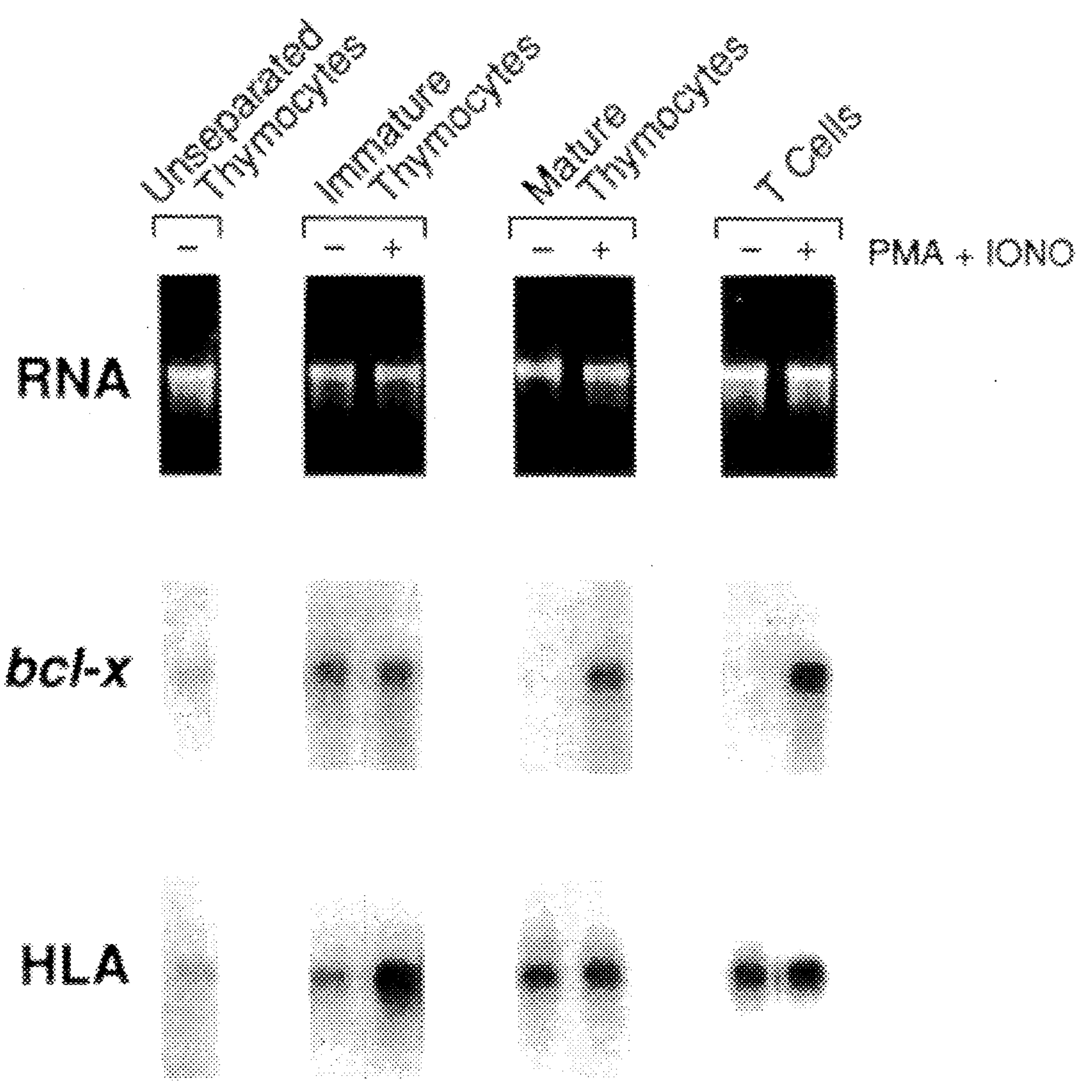
FIG. 9. Expression of bcl-x in human thymocytes and T cells. To examine the expression of bcl-x during T cell development, RNA was prepared from unseparated thymocytes, immature thymocytes, mature thymocytes, and peripheral blood T cells as described in the Experimental Procedures. The immature thymocytes, mature thymocytes, and T cell populations were further analyzed by stimulation in vitro with PMA and ionomycin for 6 to 8 hours in complete media. Resulting RNAs were isolated by the guanidinium isothiocyanate method and subjected to Northern blot analysis. Top panels demonstrate the equalization of the RNA samples used for analysis, and the lower two panels represent hybridization with a bcl-x-specific probe or an HLA class I-specific probe.

The highest level of mRNA for bcl-x in chickens was observed in the organs where lymphoid development takes place. As can be seen in FIG. 9, bcl-x mRNA can be readily detected in human thymocytes. Upon fractionation of human thymocytes into immature and mature populations, in the absence of mitogen stimulation bcl-x expression is confined to the immature "double-positive" thymocytes which express both CD4 and CD8. bcl-x mRNA was not detected n unstimulated mature "single positive" (CD4+CD8− and CD4−CD8+) thymocytes or in peripheral blood T cells.

Within the thymus, bcl-x was expressed in immature double-positive thymocytes but was not observed in freshly isolated single-positive thymocytes or peripheral blood T cells. The bcl-x mRNA species found in the double-positive thymocytes was almost exclusively of the bcl-$x_S$ form. Previous studies have shown that bcl-2 does not inhibit negative selection that normally occurs at the double-positive stage of thymocyte development (Sentman et al., 1991; Strasser et al., 1991a). The stable expression of bcl-$x_S$ at this stage of development provides a potential explanation for this observation. Nevertheless it has been shown that bcl-2 can prevent some forms of apoptosis that occur in double-positive thymocytes (Sentman et al., 1991; Strasser et al., 1991a; Seigel et al., 1991). This suggests that the influence of bcl-2 relative to bcl-$x_S$ in regulating the central events involved in apoptotic cell death may vary depending on the pathway which initiates the cell death response. Alternatively down-regulation of bcl-x expression at the mRNA or protein level may permit the effects of bcl-2 to predominate. Under these conditions it may be possible for over-expression of bcl-2 to prevent apoptotic cell death.

Although single-positive thymocytes and mature peripheral blood T cells fail to express bcl-x mRNA, both populations can be rapidly induced to express high levels of bcl-x mRNA following mitogenic activation. Again the predominant mRNA species observed encodes bcl-$x_S$. This suggests that T cell activation induces the expression of bcl-$x_S$ to increase the dependence of the cell on the growth factors provided in its local environment. Activation of peripheral T cells can render them susceptible to apoptosis (Kawabe and Ochi, 1991; Webb et al., 1990), a finding previously at odds with the upregulation of bcl-2 expression observed following T cell activation (Graninger et al., 1987; Reed et al., 1987). The inducible expression of bcl-$x_S$ in these populations may serve to regulate the amplification of T cells involved in an immune response by making them highly dependent on continuous exogenous signaling to prevent their deletion by apoptosis. Thus it appears that the differential regulation of bcl-x during T cell development and T cell activation may play a central role in regulating two important forms of apoptosis occurring in this cell lineage that were previously reported to be regulated independently of bcl-2. bcl-$x_S$ expression plays an important role in the regulation of both developmentally-and activationally-induced cell death.

Figure 10:
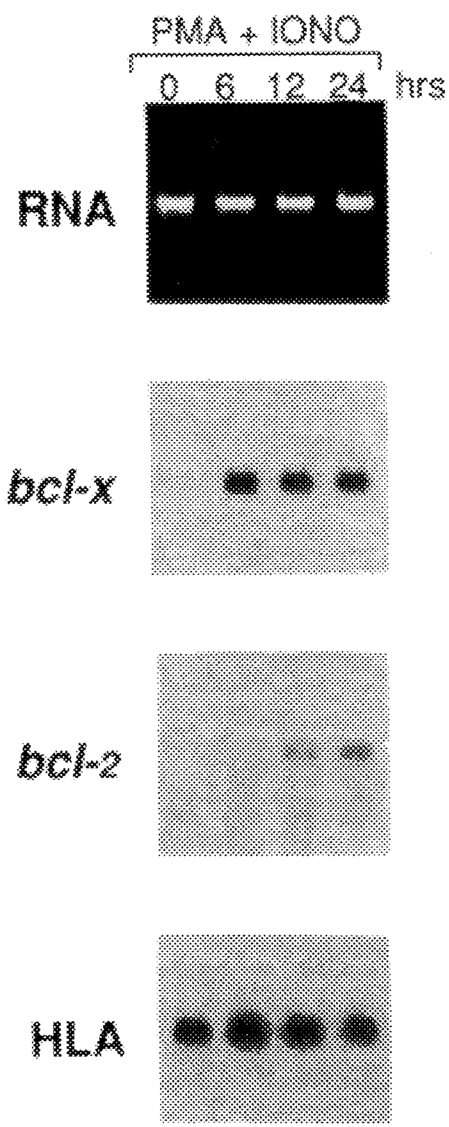
FIG. 10. Pattern of bcl-x and bcl-2 mRNA induction following peripheral blood T cell activation. Peripheral blood T cells were isolated as described in Experimental Procedures and then subjected to activation with a combination of PMA and ionomycin for 0, 6, 12, or 24 hours as indicated. The relative induction of bcl-x and bcl-2 was analyzed by equalizing RNA from the different time points for ribosomal RNA (upper panel). Duplicate Northern blots were probed for either bcl-x or bcl-2, and HLA class I mRNA. In the data shown, the bcl-x autoradiogram has been exposed for 8 hours, while the bcl-2 autoradiogram has been exposed for 15 days; both probes were of similar length and base composition.

In addition, there is a significant difference in these populations when these isolated cell populations were stimulated with the mitogenic combination of PMA and ionomycin. Six hour stimulation with PMA and ionomycin had no effect on bcl-x mRNA expression in double-positive thymocyte populations, but induced a dramatic increase in bcl-x mRNA expression in both single-positive thymocytes and peripheral blood T cells. Thus, it is likely that bcl-x mRNA is expressed constitutively in T cells with immature phenotypes that are in the process of undergoing developmental selection. Cells that have completed developmental selection down-regulate the expression of bcl-x, but bcl-x expression can be rapidly induced by T cell activation.

bcl-2 has also been reported to be induced upon T cell activation (Graninger et al., 1987; Reed et al., 1987). The kinetics of bcl-x and bcl-2 induction in peripheral blood T cells differed dramaticaly. Peripheral blood T cells were isolated at various time points after activation with a mitogenic combination of PMA and ionomycin (FIG. 10). bcl-x was rapidly induced upon activation with detectable mRNA appearing within the first 6 hours after stimulation. Thereafter, bcl-x mRNA was expressed at a relatively constant level. In contrast, bcl-2 mRNA was first detected between 6 and 12 hours after activation and underwent progressive accumulation over the first 24 hours in culture following mitogen activation. Similar results were obtained following antigen-receptor crosslinking (data not shown). Since the two probes used to detect bcl-x and bcl-2 are of similar size and GC content, we were able to estimate the differences in the steady state mRNA levels between bcl-x and bcl-2. There is approximately a 50-fold difference in the steady state accumulation of bcl-x and bcl-2 mRNA even after 24 hours of cell activation. Thus, bcl-x mRNA accumulation occurs more rapidly and to a higher steady state level than does the induction of bcl-2 mRNA upon T cell activation.

EXAMPLE VII: Tissue-Specific Expression of bcl-$x_L$ and bcl-$x_S$

Figure 11A:
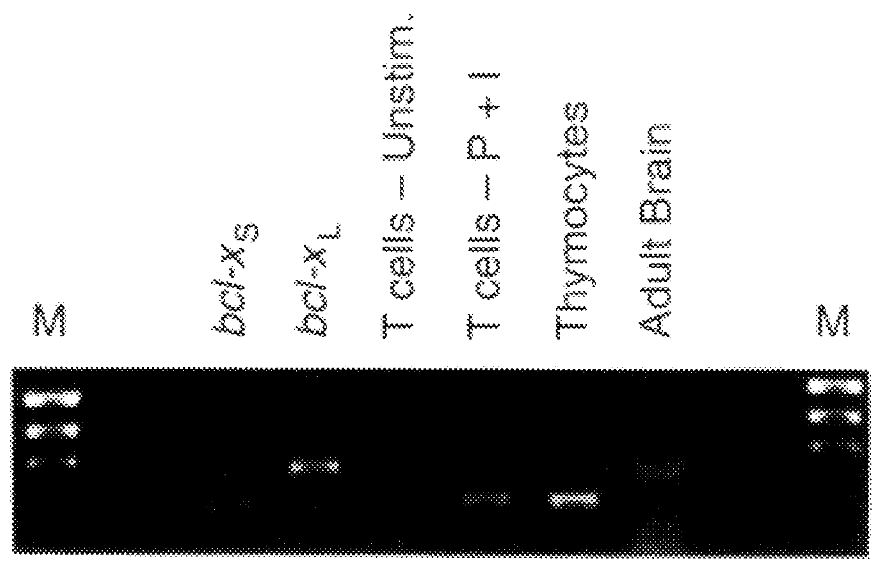
FIG. 11. Analysis of relative proportions of bcl-$x_S$ and bcl-$x_L$ mRNAs expressed in human thymocytes, T cells, and adult brain. PCR primers that flank the 5' and 3' ends of the open reading frame of bcl-$x_S$ were used to amplify bcl-$x_L$ and bcl-$x_S$ simultaneously. Using these primers, RNAs from various sources were subjected to PCR analysis. When a bcl-$x_S$ template is utilized, a single band of 591 base pairs is produced, whereas when a bcl-$x_L$ template is used a single band of 780 base pairs is observed. Molecular weight markers from HaeIII-digested fX 174 are indicated (M). A. lanes represent products from PCR reactions using a bcl-$x_S$ template, a bcl-$x_L$ template, and using RNA from unstimulated peripheral blood T cells, peripheral blood T cells stimulated for 6 hours with PMA and ionomycin, unseparated human thymocytes, and from adult brain. The identification of the observed bands in the tissue samples as bcl-$x_L$ and bcl-$x_S$ has been verified by cloning and partial sequencing of PCR products of reverse transcribed RNA from each of the tissue sources. B. A titration curve to demonstrate the validity of the PCR assay in quantitating the relative ratios of bcl-$x_L$ and bcl-$x_S$. The figure depicts the products of PCR reactions separated on 1% agarose gels and stained with ethidium bromide. The PCR was performed using a ratio of bcl-$x_L$ to bcl-$x_S$ that varied from 0:10 to 10:0 in unit increments. The resulting products reflect the relative proportions of bcl-$x_L$ and bcl-$x_S$ template added to the reaction mix.
Figure 11B:
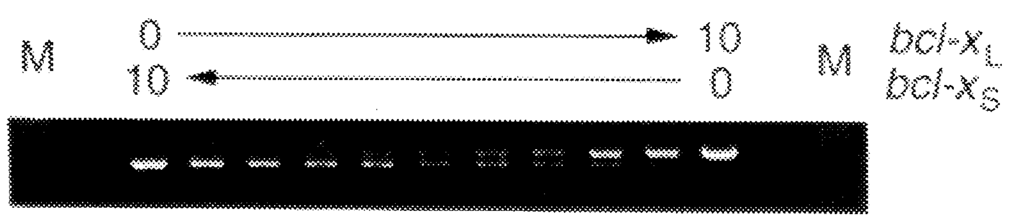

We utilized the polymerase chain reaction (PCR) to quantitate the relative abundance of the bcl-$x_L$ and bcl-$x_S$ mRNAs in a series of RNA samples obtained during T cell development and activation (FIG. 11). (U.S. PAT. NO. 4,603,102 INCORPORATED HEREIN BY REFERENCE) PCR primers that bind to sequences shared by bcl-$x_L$ and bcl-$x_S$ and that flank the region that is deleted in bcl-$x_S$ were used as primers to amplify mRNA following reverse transcription. These two primers are located on separate coding exons and therefore the product of any contaminating genomic DNA will be considerably larger than the products of the RNA species of interest. Under the conditions of the PCR reactions, the relative ratios of the two bcl-x mRNA species can be measured as demonstrated in the control experiment presented in FIG. 11B. We determined the expression of bcl-x mRNA species in unfractionated thymocytes and in peripheral blood T cells cultured in media alone or stimulated for 6 hours with PMA and ionomycin. As shown by the Northern blot analyses, resting T cells do not express bcl-x transcripts that can be identified by PCR. In contrast, activated T cells express an easily detectable PCR product comprised predominantly of the bcl-$x_S$ form. Unfractionated thymocytes also express bcl-$x_S$ mRNA almost exclusively. These data show that both activated T cells and double-positive thymocytes selectively express the form of bcl-x that enhances the dependence of the cell on exogenous signals to prevent apoptosis. This finding is consistent with the inability of overexpression of bcl-2 to overcome negative selection during the development of double-positive thymocytes as well as the failure of bcl-2 overexpression to increase significantly T cell numbers during peripheral T cell responses.

The other major tissue in chickens that demonstrated a relatively high level of bcl-x expression by Northern blot analysis was the central nervous system. PCR analysis of adult human brain mRNA shows expression exclusively of the bcl-$x_L$ mRNA species (FIG. 11A).

Thus expression of bcl-$x_L$ is correlated with the ability of adult neural tissue to maintain long term post-mitotic cell viability. Therefore, it appears that different tissues can differentially regulate both the expression and splicing of bcl-x and thus adapt the functional properties of this gene to regulate their relative sensitivity to potential mediators of apoptotic cell death.

EXAMPLE VIII: Cloning and Construction of Plasmids

Chicken bursal, spleen and thymic cDNA libraries and a genomic library that was made from red blood cells were screened with a murine bcl-2 cDNA at low stringency. The filters were hybridized in Stark's solution (50% formamide, 5x SSC [1x equals 0.15M NaCl and 0.015 sodium citrate], lx Denhardt's solution, 24 mM sodium phosphate, pH 6.5, 250 mg of RNA per ml) with 10% dextran sulfate at 42° C. overnight. The final wash conditions were 20 minutes at 42° C. in 0.1x SSC. Inserts from positive clones were subcloned into pGEM7 (Promega) and sequenced by a dideoxy termination method.

The human bcl-$x_S$ was cloned from a thymic cDNA library using a BamHI/SphI fragment of the chicken bcl-x under the hybridization and washing conditions described above. The insert was then amplified from the plaque purified phage by PCR using lgt11 primers with XbaI linker sites and pfu polymerase. The 0.84 kb amplified fragment was then subcloned into pBluescript-SK+ (Stratagene) for sequence analysis.

To clone the bcl-$x_L$ cDNA and to reclone the bcl-$x_S$ cDNA into a form to be used in functional analysis, PCR primers corresponding to sequences in the 5' untranslated region (5'-TTGGACAATGGACTGGTTGA-3') and the 3' untranslated region (5'-GTAGAGTGGATGGTCAGTG-3') of the bcl-$x_S$ cDNA were synthesized. The primers contained EcoRI linkers for subcloning and were used to amplify clones from cDNA libraries prepared from human T cells, the T cell line Jurkat, and human brain. The phage (107 pfu) were boiled for 5 minutes in 25 ml of water prior to the PCR reactions (1.25 minutes at 94° C., 2 minutes at 56° C., 3 minutes at 72° C.×35 cycles). Bands of appropriate size (0.8 kb for bcl-$x_L$ and 0.6 kb for bcl-$x_S$) that could hybridize to the bcl-$x_S$ cDNA were subcloned into the EcoRI site of pBluescript-SK+ for sequence analysis and production of in vitro transcription and translation products. For transfection and subsequent functional assays, the bcl-$x_L$ and bcl-$x_S$ inserts were excised from pBluescript SK+ and subcloned into the EcoRI site of pSFFV-Neo (Neo;Fuhlbrigge et at., 1988). Orientation of the inserts was determined by restriction enzyme mapping and plasmids with inserts in the forward orientation were designated pSFFV-Neo-bcl-$x_L$ (bcl-$x_L$) and pSFFV-Neo-bcl-$x_S$ (bcl-$x_S$), while plasmids with inserts in the reverse orientation were named pSFFV-Neo-bcl-$x_L$rev (bcl-$x_L$rev) and pSFFV-Neo-bcl-$x_S$rev (bcl-$x_S$rev).

Sequence comparisons and peptide analyses were performed with the University of Wisconsin Genetics Computer Group programs: FASTA, TFASTA, PILEUP, PEPTIDESTRUCTURE, and GAP. The nucleotide sequences of chicken bcl-x, human bcl-$x_L$, and human bcl-$x_S$ have been sent to the GenBank database.

EXAMPLE IX: Southern Blot Analysis

Genomic DNA from chicken mouse, and human lymphoid cells was isolated by standard methods, as previously described (Thompson and Neiman, 1987). The DNA was quantitated and 10 mg was digested with indicated restriction enzymes overnight. Digested DNA was separated on a 1% agarose gel and blotted onto nitrocellulose. Blots were hybridized as described above with either an SphI/BamHI fragment of chicken bcl-x or a HindIII/BamHI fragment from the first coding exon of mouse bcl-2. Washing conditions were as described above.

EXAMPLE X: Cell Isolation and RNA Analysis

For the chicken tissue Northern blots, newly hatched chicks were sacrificed and RNA was isolated from the indicated tissues by a guanidinium isothiocyanate method followed by centrifugation through a cesium chloride gradient as previously described (Thompson et al., 1986). RNA was equalized to the 28S ribosomal RNA, separated on agarose/formaldehyde gels and subsequently blotted onto nitrocellulose. The blots were probed with the SphI/BamHI chicken bcl-x fragment. Blots were then stripped by boiling and hybridized with the HindIII/BamHI mouse bcl-2 probe.

Human T cells were isolated from healthy donors by leukophoresis, followed by density gradient centrifugation. CD28-positive T cells were negatively selected via an immunomagnetic procedure (June et al., 1987). RNA was then isolated from T cells that were either resting or activated with phorbol myristate acetate (PMA; 10 ng/ml) and ionomycin (0.8 mg/ml) for the indicated times. RNA was equalized and subjected to electrophoresis through agarose/formaldehyde denaturing gels and the gels were then blotted as described above. Duplicate blots were probed with the human bcl-$x_S$ cDNA or the mouse bcl-2 exon II fragment and a human HLA class I cDNA. Final washing conditions were 0.1xSSC, 0.1% SDS for 20 minutes at 56° C.

Human thymocytes were isolated from surgical pathology specimens from children under the age of three who had undergone cardiothoracic surgery. Thymic tissue was passed through nylon mesh to obtain a single cell suspension followed by separation of mononuclear cells on a ficoll-hypaque cushion. RNA was then extracted from either resting or PMA and Ionomycin stimulated cells and subjected to Northern blot analysis. To determine if bcl-x expression was regulated during thymocyte development, thymocytes were separated into mature ("single-positive" cells) and immature ("double-positive") subpopulations prior to stimulation and RNA extraction as previously described (Turka et al., 1991). Thymocyte fractionation was performed by negative immunomagnetic selection. Immature thymocytes were prepared by removal of cells expressing high levels of CD28, while mature thymocytes were selected by the removal of CD 1+cells. The expression status of the resulting cells for CD4 and CD8 confirmed that greater that 90% of the immature population expressed CD4 and CD8 while greater that 95% of the mature population were single-positive cells.

To determine which form of bcl-x mRNA was being expressed, 1 mg of total cellular RNA or 0.1 mg of polyA+ RNA from the various sources was reversed transcribed with AMV reverse transcriptase for 1 hour at 42° C. Twenty percent of the cDNA product was then subjected to PCR using the 5' and 3' primers and amplification conditions described above. Because the two primers are each located on separate coding exons, the amplification product of contaminating genomic DNA will be much larger than the product of either of the two RNA species, bcl-$x_L$ and bcl-$x_S$. To assure that the PCR conditions were not biased to one form of the cDNA, concurrent PCR reactions were run with plasmids containing bcl-$x_L$ or bcl-$x_S$ alone or mixed in various ratios.

EXAMPLE XI: Cell Transfection and Functional Studies

Murine FL5.12 cells were cultured as previously described (Hockenbery et al., 1990; Nuñez et al., 1990). Cells were transfected by electroporation (200 V, 960 mF) with the pSFFV-Neo plasmid containing either bcl-2a (bcl-2), bcl-$x_L$ in both transcriptional orientations (bcl-$x_L$ and bcl-$x_L$rev), and bcl-$x_S$ in both transcriptional orientations (bcl-$x_S$ and bcl-$x_S$rev). As a control, transfections were also performed with the pSFFV-Neo plasmid without an insert (Neo). Transfectants were selected for the acquisition of neomycin resistance by growth in the presence of G418 (1 mg/ml). Bulk transfectants and single cell clones (generated by limiting dilution) were maintained by growth in media supplemented with IL-3 as previously described (Nuñez et al., 1990). To assess cell survival, cells were first grown at 2×105/ml in the presence of an optimal concentration of growth factor for 20–24 hours. The cells were then washed with RPMI 1640 medium three times to remove any residual IL-3, and plated at 105 cells per well in 96 well culture dishes in medium supplemented with 10% fetal calf serum. Cell survival was determined at the indicated time points by trypan blue exclusion. To confirm that cell death was due to apoptosis, transfected cells (2×106) were isolated 0, 8, 24, and 48 hours after growth factor removal and lysed in 1.0% SDS, 100 mM NaCl, 10 mM Tris pH 8.0, 1 mM EDTA, and 200 mg/ml proteinase K for 2 hours at 50° C. Following incubation, samples were treated with RNase A (20 mg/ml) for 2 hours at 37° C., phenol/chloroform extracted, and ethanol precipitated. DNA was then separated on a 1.2% agarose gel and stained with ethidium bromide.

BCL-2 specific antibody did not cross react with BCL-X. Cells were washed and fixed with 1% paraformaldehyde for 10 minutes at room temperature, then stained with the 6C8 monoclonal antibody, a hamster monoclonal antibody specific for human bcl-2 (Hockenbery et al., 1990), or an isotype-matched hamster antibody control in 0.3% saponin in PBS for 30 minutes at 4° C. Cells were washed in 0.03% saponin/PBS and incubated with biotinylated F(ab')2 goat anti-hamster IgG for 30 minutes at 4° C. Cells were washed in 0.03% saponin/PBS and incubated with RED 670-streptavidin and analyzed by flow cytometry. Analysis of bcl-$x_L$- and bcl-$x_S$-transfected cells showed that the bcl-2-specific antibody did not crossreact with the BCL-X expressed in these cells. bcl-x expression was confirmed by Northern blot analysis, with b-actin expression utilized as a loading control.

EXAMPLE XII: In vitro Transcription and Translation of bcl-x pBluescript-SK+plasmids containing bcl-$x_L$ and bcl-$x_S$ were linearized at the 3' multiple cloning site with XbaI and BamHI respectively and transcribed with T7 RNA polymerase for 1 hour at 37° C. bcl-$x_L$ was also linearized at the 5' multiple cloning site with XhoI and transcribed with T3 polymerase as an antisense control. The resulting run-off transcripts (bcl-$x_L$, bcl-$x_S$ and bcl-$x_S$-as) were phenol/chloroform extracted and ethanol precipitated. In vitro translation was then performed with a rabbit reticulocyte lysate kit (Promega) in the presence of 35S-methionine for 1 hour at 30° C. Five ml of lysate was added to SDS loading buffer and subjected to SDS-PAGE (15% gel). Gels were dried and exposed to x-ray film.

Because numerous modifications and variations in the practice of the present invention are expected to occur to those skilled in the art, only such limitations as appear in the appended claims should be placed thereon.

REFERENCES CITED

The references listed below as well as all references cited in the specification are incorporated herein by reference to the extent that they supplement, explain, provide a background for or teach methodology, techniques and/or compositions employed herein.

Adelman et al. (1983) *DNA* 2:183.

Allsopp et al. (1993) *Cell* 73:295.

Bakhshi et al. (1985) *Cell* 41:899.

Blackman et al. (1990) *Science* 248:1335.

Bolivar et al., (1977) *Gene,* 2:95.

Borzillo et al. (1992) *Oncogene* 7:869.

Boshart et al. (1985) *Cell* 41:521.

Cazals-Hatem et al. (1992) *Biochim. Biophys. Acta* 1132:109.

Chang et al., (1978) *Nature,* 375:615.

Chen-Levy, Z. and Cleary, M. L. (1990) *J. Biol. Chem* 265:4929.

Chen-Levy et al. (1989) *Mol. Cell. Biol.* 9:701.

Cleary et al. (1986) *Cell* 47:19.

Cooper et al. (1991) *Adv. Immunol.* 50:87.

Cowan et al. (1984) *Science* 225:1258.

Crea et al., (1978) *Proc. Natl. Acad. Sci. U.S.A,* 75:5765.

Cuende et al. (1993) *EMBO J.* 12: 1555.

Davies, A.M. (1987)*Development* 101:185.

Eguchi et al. (1992) *Nucl. Acids Res.* 20:4187.

Ellis et al (1991) *Annu. Rev. Cell Biol.* 7:663.

Ferruti, P. and Tanzi, M. C., (1986) *Cris. Rev. Ther. Drug Carrier Syst.* 2:117–136.

Fiers et al., (1978) *Nature* 273:113.

Fuhlbrigge et al. (1988) *Proc. Natl. Acad. Sci. USA* 85:5649.

Gabizon, A. et al., (1990) *Cancer Res.* 50:6371–6378

Garcia et al. (1992) *Science* 258:302.

Goeddel et al., (1979) *Nature,* 281:544.

Goeddel et al., (1980) *Nucleic Acids Res.,* 8:4057.

Graninger et al. (1987) *J. Clin. Invest.* 80:1512.

Hess et al., (1968) *J. Adv. Enzyme Reg.* 7:149.

Hitzeman et al., (1980)*J. Biol. Chem.* 255:2073.

Hockenbery et al. (1990) *Nature* 348:334.

Holland et al., (1978) *Biochemistry* 17:4900.

Itakura et al., (1977) *Science,* 198:1056.

Jones, (1977) *Genetics* 85:12.

June et al. (1987) *Mol. Cell. Biol.* 7:4472.

Kawabe, Y. and Ochi, A. (1991) *Nature* 349:245.

Kerr et al. (1972) *Br. J. Cancer* 26:239.

Kingsman et al., (1979) *Gene* 7:141.

Kruse and Patterson, eds. (1973) *Tissue Culture*, Academic Press.

Kyte, J., and R. F. Doolittle (1982) *J. Mol. Biol.* 157: 105.

Messing et al., Third Cleveland Symposium on Macromolecules and Recombinant DNA, Editor A. Walton, Elsevier, Amsterdam (1981).

McDonnell et al. (1989) *Cell* 57:79.

Murphy et al. (1990) *Science* 250:1720.

Negrini et al (1987) *Cell* 49:455.

Neiman et al. (1991) *Proc. Natl. Acad. Sci. USA* 88:5857.

Nunez et al. (1990) *J. Immunol.* 144:3602.

Okayarea et al. (1983) *Mol. Cell Biol.* 3:280.

Oppenheim, R. W. (1991)*Annu. Rev. Neurosci.* 14:453.

Raff, M. C. (1992) *Nature* 356:397.

Ranade, V. V. (1989)*J. Clin. Pharmacol.* 29:685–694

Reed et al. (1987) *Science* 236:1295.

Rothenberg, E. V. (1992)*Adv. Immunol.* 51:85.

Sambrook, J. et al. (1989) *Molecular Cloning: A Laboratory Manual* (Cold Spring Harbor Laboratory Press, Cold Spring Harbor, N.Y.).

Seeburg (1982) *DNA* 1:239.

Sentman et al. (1991) *Cell* 67:879.

Siebwenlist et al., (1980) *Cell,* 20:269.

Siegel, et al. (1992) *Proc. Natl. Acad. Sci.* USA 89:7003.

Stinchcomb et al., (1979) *Nature,* 282:39.

Stratford-Perricaudet et al. (1992).

Strasser et al (1991a) *Cell* 67:889.

Strasser et al. (1991b) *Proc. Natl. Acad. Sci. USA* 88:8661.

Thompson et al. (1986) *Nature* 319:374.

Thompson, C. B. and Neiman, P.E. (1987) *Cell* 48:369.

Thomsen et al. (1984) *PNAS* 81:659.

Tschemper et al., (1980) *Gene* 10:157.

Tsujimoto, Y. and Croce, C. M. (1986) *Proc. Natl. Acad. Sci. USA* 83:5214.

Turka et al. (1991) *J. Immunol.* 146:1428.

Vaux et al. (1988) *Nature* 335440.

Webb et al (1990) *Cell* 63: 1249.

Williams, G. T. (1991) *Cell* 65: 1097.

Wyllie et al. (1980) *Int. Rev. Cytol.* 68:251.

What is claimed is:

1. An isolated and purified polynucleotide that encodes BCL-$X_L$.

2. The isolated and purified polynucleotide of claim 1, wherein said polynucleotide is a DNA molecule.

3. The DNA molecule of claim 2, wherein said encoded polypeptide comprises the amino acid residue sequence of SEQ ID NO:2 or SEQ ID NO:6.

4. The isolated and purified polynucleotide of claim 1, wherein said polynucleotide comprises the nucleotide base sequence of SEQ ID NO:1 or SEQ ID NO:5.

5. An isolated and purified polynueleotide comprising a base sequence that is identical or complementary to a segment of at least 25 contiguous bases of SEQ ID NO: 1 or SEQ ID NO:5, wherein said polynucleotide hybridizes to the sequence of SEQ ID NO:1 or SEQ ID NO:5.

6. An expression vector comprising a polynucleotide that encodes BCL-$X_L$.

7. The expression vector of claim 6, wherein the polynucleotide is operatively linked to an enhancer-promoter.

8. A recombinant host cell transfected with a polynucleotide that encodes BCL-$X_L$.

9. The recombinant host cell of claim 8 where the polynucleotide is under the transcriptional control of regulatory signals functional in the recombinant host cell, wherein the regulatory signals appropriately control expression of said polypeptide in a manner to enable all necessary transcriptional and post-transcriptional modification.

10. A process of using a polynucleotide in accordance with claim 1 comprising:

(a) transfecting a cell with a polynucleotide in accordance with claim 1 to produce a transformed host cell; and (b) maintaining the transformed host cell under biological conditions sufficient for expression of the polypeptide.

11. The polynucleotide of claim 1, further defined as a recombinant vector.

12. The polynucleotide of claim 5, further defined as a recombinant vector.

* * * * *

UNITED STATES PATENT AND TRADEMARK OFFICE

CERTIFICATE OF CORRECTION

PATENT NO. : 5,646,008

DATED : July 8, 1997

INVENTOR(S) : Craig B. Thompson, Lawrence H. Boise and Gabriel Nunez

It is certified that error appears in the above-identified patent and that said Letters Patent is hereby corrected as shown below:

Title page, item [73], insert --Arch Development Corporation, Chicago, Illinois--.

Signed and Sealed this

Twenty-fourth Day of March, 1998

Attest:

BRUCE LEHMAN

*Attesting Officer* *Commissioner of Patents and Trademarks*

UNITED STATES PATENT AND TRADEMARK OFFICE

CERTIFICATE OF CORRECTION

PATENT NO. : 5,646,008

DATED : July 8, 1997

INVENTOR(S) : Craig B. Thopson et al.

It is certified that error appears in the above-identified patent and that said Letters Patent is hereby corrected as shown below:

Column 1, line 3, insert the following:

The Government may have rights in the invention pursuant to a funding agreement under 35 U.S.C. § 202(c)(4): NIH Grant No. AR20577.

Signed and Sealed this

Twenty-first Day of December, 1999

Attest:

Q. TODD DICKINSON

*Attesting Officer* *Acting Commissioner of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 1303 base pairs
( B ) TYPE: nucleic acid
( C ) STRANDEDNESS: single
( D ) TOPOLOGY: unknown ( i i ) MOLECULE TYPE: DNA (genomic)

( i x ) FEATURE:
( A ) NAME/KEY: CDS
( B ) LOCATION: 179..751

( x i ) SEQUENCE DESCRIPTION: SEQ ID NO:1:

```
GGCGCCAGCA AGCTGTCGTG TTAACCGTTT CCTTGCCTCT CTTTTCCTCT CTGCCTGTCT      60

GTGCAAAGGT CGGATGTGTT CGCCGGTCAC GAGGGAGCGT GGAGCCAGGA GCTGCTAAGT     120

GTGCTCATCT GCTCGTGCAC TGGACCATGG ACTCATTGAG GGCGTCTCAG GTGTGAAA       178

ATG TCC AGC AGT AAC CGG GAG TTA GTG ATT GAC TTT GTT TCC TAC AAG       226
Met Ser Ser Ser Asn Arg Glu Leu Val Ile Asp Phe Val Ser Tyr Lys
  1               5                  10                  15

CTC TCG CAG AGG GGG CAC TGC TGG AGC GAG CTG GAG GAA GAG GAT GAG       274
Leu Ser Gln Arg Gly His Cys Trp Ser Glu Leu Glu Glu Glu Asp Glu
             20                  25                  30

AAC AGG ACT GAC ACT GCA GCT GAG GCA GAG ATG GAC AGC GTC CTC AAT       322
Asn Arg Thr Asp Thr Ala Ala Glu Ala Glu Met Asp Ser Val Leu Asn
         35                  40                  45

GGG AGC CCA TCC TGG CAC CCC CCT GCC GGC CAC GTA GTG AAC GGA GCC       370
Gly Ser Pro Ser Trp His Pro Pro Ala Gly His Val Val Asn Gly Ala
     50                  55                  60

ACC GTG CAC CGG AGC AGC CTG GAA GTT CAT GAA ATT GTT CGA GCA TCC       418
Thr Val His Arg Ser Ser Leu Glu Val His Glu Ile Val Arg Ala Ser
 65                  70                  75                  80

GAC GTG AGG CAG GCG CTG AGA GAT GCG GGG GAT GAG TTT GAG CTG AGG       466
Asp Val Arg Gln Ala Leu Arg Asp Ala Gly Asp Glu Phe Glu Leu Arg
                 85                  90                  95

TAC CGG AGG GCT TTC AGC GAC CTC ACC TCC CAG CTC CAC ATC ACC CCT       514
Tyr Arg Arg Ala Phe Ser Asp Leu Thr Ser Gln Leu His Ile Thr Pro
            100                 105                 110

GGC ACG GCG TAC CAG AGC TTT GAG CAG GTA GTG AAT GAA CTC TTC CAT       562
Gly Thr Ala Tyr Gln Ser Phe Glu Gln Val Val Asn Glu Leu Phe His
        115                 120                 125

GAT GGT GTG AAC TGG GGG CGC ATC GTG GCT TTC TTC TCC TTC GGA GGG       610
Asp Gly Val Asn Trp Gly Arg Ile Val Ala Phe Phe Ser Phe Gly Gly
    130                 135                 140

GCT TTG TGC GTG GAG AGC GTG GAC AAG GAG ATG CGG GTA CTG GTG GGA       658
Ala Leu Cys Val Glu Ser Val Asp Lys Glu Met Arg Val Leu Val Gly
145                 150                 155                 160

CGC ATT GTG TCT TGG ATG ACC ACG TAC TTG ACC GAC CAT CTA GAT CCC       706
Arg Ile Val Ser Trp Met Thr Thr Tyr Leu Thr Asp His Leu Asp Pro
                165                 170                 175

TGG ATC CAG GAG AAT GGC GGC TGG GTA AGA ACT GCT CTC CCA TAGGGATGGC    758
Trp Ile Gln Glu Asn Gly Gly Trp Val Arg Thr Ala Leu Pro
            180                 185                 190

TCCCTGCATC CTAGCTCAAG GCCAGCGGCG GTGCTGGCCA GATCAAGCAG CCTTCAGTGA     818
```

-continued

TTGTGCTTGT GCTTGGTCTA CACCTTGCAG GGCAATAAAT TGGTACGTGG CCCTTCCCTC 878

TTCATTCTTA ATGCTCTGCT GCAAGAGGGT CAGTCCACTG TGTTGAAACA AAGAGTTAAC 938

ATTCTGATTT GTCCTCCTGC ATCCCTTTTT CTCCTCCTTC TCCCTGGCTG TTACATAAGA 998

GACCCATTTT CCGAGAGCCT GTGGAAATGT AATGTCATCC AAGCTTGTTC TTCAAATGGG 1058

AGCCCTTGCT CTTGGGCATG TTCCTCATGT CATTTAACAG CAGGGAGTGG AGCTTCCTCC 1118

CCTCCGTGCT CAGCAGTGTT CCAGCCTGGC CCTGTGATCT GGTGGGGTAA CAGCTACTTC 1178

TTCATTCTGG AGATGGGACG ATGTCTGCCG CTGCCATCGC GTGGAGTGAA TCCTGCAGCA 1238

GCTCTCTGTG GGTAGGGCTG CTGGGACGCA TCACAGGGAG CGGTGCACCC AGCGCGCAGG 1298

AATTC 1303

( 2 ) INFORMATION FOR SEQ ID NO:2:

( i ) SEQUENCE CHARACTERISTICS:
( A ) LENGTH: 190 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met Ser Ser Ser Asn Arg Glu Leu Val Ile Asp Phe Val Ser Tyr Lys
1 5 10 15

Leu Ser Gln Arg Gly His Cys Trp Ser Glu Leu Glu Glu Glu Asp Glu
20 25 30

Asn Arg Thr Asp Thr Ala Ala Glu Ala Glu Met Asp Ser Val Leu Asn
35 40 45

Gly Ser Pro Ser Trp His Pro Pro Ala Gly His Val Val Asn Gly Ala
50 55 60

Thr Val His Arg Ser Ser Leu Glu Val His Glu Ile Val Arg Ala Ser
65 70 75 80

Asp Val Arg Gln Ala Leu Arg Asp Ala Gly Asp Glu Phe Glu Leu Arg
85 90 95

Tyr Arg Arg Ala Phe Ser Asp Leu Thr Ser Gln Leu His Ile Thr Pro
100 105 110

Gly Thr Ala Tyr Gln Ser Phe Glu Gln Val Val Asn Glu Leu Phe His
115 120 125

Asp Gly Val Asn Trp Gly Arg Ile Val Ala Phe Phe Ser Phe Gly Gly
130 135 140

Ala Leu Cys Val Glu Ser Val Asp Lys Glu Met Arg Val Leu Val Gly
145 150 155 160

Arg Ile Val Ser Trp Met Thr Thr Tyr Leu Thr Asp His Leu Asp Pro
165 170 175

Trp Ile Gln Glu Asn Gly Gly Trp Val Arg Thr Ala Leu Pro
180 185 190

( 2 ) INFORMATION FOR SEQ ID NO:3:

( i ) SEQUENCE CHARACTERISTICS:
( A ) LENGTH: 63 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

Val Val Asn Glu Leu Phe Arg Asp Gly Val Asn Trp Gly Arg Ile Val

-continued

```
1               5                   10                  15

Ala Phe Phe Ser Phe Gly Gly Ala Leu Cys Val Glu Ser Val Asp Lys
            20                  25                  30

Glu Met Gln Val Leu Val Ser Arg Ile Ala Ala Trp Met Ala Thr Tyr
        35                  40                  45

Leu Asn Asp His Leu Glu Pro Trp Ile Gln Glu Asn Gly Gly Trp
    50                  55                  60
```

( 2 ) INFORMATION FOR SEQ ID NO:4:

( i ) SEQUENCE CHARACTERISTICS:
( A ) LENGTH: 205 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:4:

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Ala
                85                  90                  95

Leu Arg Gln Ala Gly Asp Asp Phe Ser Arg Arg Tyr Arg Gly Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Val Gly Ala Ser Gly Asp Val Ser Leu Gly
        195                 200                 205
```

( 2 ) INFORMATION FOR SEQ ID NO:5:

( i ) SEQUENCE CHARACTERISTICS:
( A ) LENGTH: 926 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 135..836

( x i ) SEQUENCE DESCRIPTION: SEQ ID NO:5:

-continued

```
GAATCTCTTT CTCTCCCTTC AGAATCTTAT CTTGGCTTTG GATCTTAGAA GAGAATCACT    60

AACCAGAGAC GAGACTCAGT GAGTGAGCAG GTGTTTTGGA CAATGGACTG GTTGAGCCCA   120

TCCCTATTAT AAAA ATG TCT CAG AGC AAC CGG GAG CTG GTG GTT GAC TTT     170
                Met Ser Gln Ser Asn Arg Glu Leu Val Val Asp Phe
                 1               5                  10

CTC TCC TAC AAG CTT TCC CAG AAA GGA TAC AGC TGG AGT CAG TTT AGT     218
Leu Ser Tyr Lys Leu Ser Gln Lys Gly Tyr Ser Trp Ser Gln Phe Ser
         15                  20                  25

GAT GTG GAA GAG AAC AGG ACT GAG GCC CCA GAA GGG ACT GAA TCG GAG     266
Asp Val Glu Glu Asn Arg Thr Glu Ala Pro Glu Gly Thr Glu Ser Glu
     30                  35                  40

ATG GAG ACC CCC AGT GCC ATC AAT GGC AAC CCA TCC TGG CAC CTG GCA     314
Met Glu Thr Pro Ser Ala Ile Asn Gly Asn Pro Ser Trp His Leu Ala
 45                  50                  55                  60

GAC AGC CCC GCG GTG AAT GGA GCC ACT GCG CAC AGC AGC AGT TTG GAT     362
Asp Ser Pro Ala Val Asn Gly Ala Thr Ala His Ser Ser Ser Leu Asp
                 65                  70                  75

GCC CGG GAG GTG ATC CCC ATG GCA GCA GTA AAG CAA GCG CTG AGG GAG     410
Ala Arg Glu Val Ile Pro Met Ala Ala Val Lys Gln Ala Leu Arg Glu
             80                  85                  90

GCA GGC GAC GAG TTT GAA CTG CGG TAC CGG CGG GCA TTC AGT GAC CTG     458
Ala Gly Asp Glu Phe Glu Leu Arg Tyr Arg Arg Ala Phe Ser Asp Leu
         95                 100                 105

ACA TCC CAG CTC CAC ATC ACC CCA GGG ACA GCA TAT CAG AGC TTT GAA     506
Thr Ser Gln Leu His Ile Thr Pro Gly Thr Ala Tyr Gln Ser Phe Glu
    110                 115                 120

CAG GTA GTG AAT GAA CTC TTC CGG GAT GGG GTA AAC TGG GGT CGC ATT     554
Gln Val Val Asn Glu Leu Phe Arg Asp Gly Val Asn Trp Gly Arg Ile
125                 130                 135                 140

GTG GCC TTT TTC TCC TTC GGC GGG GCA CTG TGC GTG GAA AGC GTA GAC     602
Val Ala Phe Phe Ser Phe Gly Gly Ala Leu Cys Val Glu Ser Val Asp
                145                 150                 155

AAG GAG ATG CAG GTA TTG GTG AGT CGG ATC GCA GCT TGG ATG GCC ACT     650
Lys Glu Met Gln Val Leu Val Ser Arg Ile Ala Ala Trp Met Ala Thr
            160                 165                 170

TAC CTG AAT GAC CAC CTA GAG CCT TGG ATC CAG GAG AAC GGC GGC TGG     698
Tyr Leu Asn Asp His Leu Glu Pro Trp Ile Gln Glu Asn Gly Gly Trp
        175                 180                 185

GAT ACT TTT GTG GAA CTC TAT GGG AAC AAT GCA GCA GCC GAG AGC CGA     746
Asp Thr Phe Val Glu Leu Tyr Gly Asn Asn Ala Ala Ala Glu Ser Arg
    190                 195                 200

AAG GGC CAG GAA CGC TTC AAC CGC TGG TTC CTG ACG GGC ATG ACT GTG     794
Lys Gly Gln Glu Arg Phe Asn Arg Trp Phe Leu Thr Gly Met Thr Val
205                 210                 215                 220

GCC GGC GTG GTT CTG CTG GGC TCA CTC TTC AGT CGG AAA TGACCAGACA      843
Ala Gly Val Val Leu Leu Gly Ser Leu Phe Ser Arg Lys
                225                 230

CTGACCATCC ACTCTACCCT CCCACCCCCT TCTCTGCTCC ACCACATCCT CCGTCCAGCC   903

GCCATTGCCA CCAGGAGAAC CCG                                           926
```

( 2 ) INFORMATION FOR SEQ ID NO:6:

( i ) SEQUENCE CHARACTERISTICS:
( A ) LENGTH: 233 amino acids
( B ) TYPE: amino acid
( D ) TOPOLOGY: linear ( i i ) MOLECULE TYPE: protein ( x i ) SEQUENCE DESCRIPTION: SEQ ID NO:6:

-continued

```
Met Ser Gln Ser Asn Arg Glu Leu Val Val Asp Phe Leu Ser Tyr Lys
  1               5                  10                  15

Leu Ser Gln Lys Gly Tyr Ser Trp Ser Gln Phe Ser Asp Val Glu Glu
             20                  25                  30

Asn Arg Thr Glu Ala Pro Glu Gly Thr Glu Ser Glu Met Glu Thr Pro
         35                  40                  45

Ser Ala Ile Asn Gly Asn Pro Ser Trp His Leu Ala Asp Ser Pro Ala
     50                  55                  60

Val Asn Gly Ala Thr Ala His Ser Ser Ser Leu Asp Ala Arg Glu Val
 65                  70                  75                  80

Ile Pro Met Ala Ala Val Lys Gln Ala Leu Arg Glu Ala Gly Asp Glu
                 85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230
```

( 2 ) INFORMATION FOR SEQ ID NO:7:

( i ) SEQUENCE CHARACTERISTICS:
( A ) LENGTH: 737 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 135..647

( x i ) SEQUENCE DESCRIPTION: SEQ ID NO:7:

```
GAATCTCTTT CTCTCCCTTC AGAATCTTAT CTTGGCTTTG GATCTTAGAA GAGAATCACT       60

AACCAGAGAC GAGACTCAGT GAGTGAGCAG GTGTTTTGGA CAATGGACTG GTTGAGCCCA      120

TCCCTATTAT AAAA ATG TCT CAG AGC AAC CGG GAG CTG GTG GTT GAC TTT        170
                Met Ser Gln Ser Asn Arg Glu Leu Val Val Asp Phe
                  1               5                  10

CTC TCC TAC AAG CTT TCC CAG AAA GGA TAC AGC TGG AGT CAG TTT AGT        218
Leu Ser Tyr Lys Leu Ser Gln Lys Gly Tyr Ser Trp Ser Gln Phe Ser
         15                  20                  25

GAT GTG GAA GAG AAC AGG ACT GAG GCC CCA GAA GGG ACT GAA TCG GAG        266
Asp Val Glu Glu Asn Arg Thr Glu Ala Pro Glu Gly Thr Glu Ser Glu
     30                  35                  40

ATG GAG ACC CCC AGT GCC ATC AAT GGC AAC CCA TCC TGG CAC CTG GCA        314
Met Glu Thr Pro Ser Ala Ile Asn Gly Asn Pro Ser Trp His Leu Ala
```

-continued

```
 45                       50                       55                       60

GAC AGC CCC GCG GTG AAT GGA GCC ACT GCG CAC AGC AGC AGT TTG GAT      362
Asp Ser Pro Ala Val Asn Gly Ala Thr Ala His Ser Ser Ser Leu Asp
                 65                      70                      75

GCC CGG GAG GTG ATC CCC ATG GCA GCA GTA AAG CAA GCG CTG AGG GAG      410
Ala Arg Glu Val Ile Pro Met Ala Ala Val Lys Gln Ala Leu Arg Glu
             80                      85                      90

GCA GGC GAC GAG TTT GAA CTG CGG TAC CGG CGG GCA TTC AGT GAC CTG      458
Ala Gly Asp Glu Phe Glu Leu Arg Tyr Arg Arg Ala Phe Ser Asp Leu
         95                     100                     105

ACA TCC CAG CTC CAC ATC ACC CCA GGG ACA GCA TAT CAG AGC TTT GAA      506
Thr Ser Gln Leu His Ile Thr Pro Gly Thr Ala Tyr Gln Ser Phe Glu
    110                     115                     120

CAG GAT ACT TTT GTG GAA CTC TAT GGG AAC AAT GCA GCA GCC GAG AGC      554
Gln Asp Thr Phe Val Glu Leu Tyr Gly Asn Asn Ala Ala Ala Glu Ser
125                     130                     135                     140

CGA AAG GGC CAG GAA CGC TTC AAC CGC TGG TTC CTG ACG GGC ATG ACT      602
Arg Lys Gly Gln Glu Arg Phe Asn Arg Trp Phe Leu Thr Gly Met Thr
                145                     150                     155

 GTG GCC GGC GTG GTT CTG CTG GGC TCA CTC TTC AGT CGG AAA TGACCAGACA  654
Val Ala Gly Val Val Leu Leu Gly Ser Leu Phe Ser Arg Lys
            160                     165                     170

CTGACCATCC ACTCTACCCT CCCACCCCCT TCTCTGCTCC ACCACATCCT CCGTCCAGCC    714

GCCATTGCCA CCAGGAGAAC CCG                                            737
```

( 2 ) INFORMATION FOR SEQ ID NO:8:

( i ) SEQUENCE CHARACTERISTICS:
( A ) LENGTH: 170 amino acids
( B ) TYPE: amino acid
( D ) TOPOLOGY: linear ( i i ) MOLECULE TYPE: protein ( x i ) SEQUENCE DESCRIPTION: SEQ ID NO:8:

```
Met Ser Gln Ser Asn Arg Glu Leu Val Val Asp Phe Leu Ser Tyr Lys
  1               5                  10                  15

Leu Ser Gln Lys Gly Tyr Ser Trp Ser Gln Phe Ser Asp Val Glu Glu
             20                  25                  30

Asn Arg Thr Glu Ala Pro Glu Gly Thr Glu Ser Glu Met Glu Thr Pro
         35                  40                  45

Ser Ala Ile Asn Gly Asn Pro Ser Trp His Leu Ala Asp Ser Pro Ala
     50                  55                  60

Val Asn Gly Ala Thr Ala His Ser Ser Ser Leu Asp Ala Arg Glu Val
 65                  70                  75                  80

Ile Pro Met Ala Ala Val Lys Gln Ala Leu Arg Glu Ala Gly Asp Glu
                 85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Asp Thr Phe
        115                 120                 125

Val Glu Leu Tyr Gly Asn Asn Ala Ala Ala Glu Ser Arg Lys Gly Gln
    130                 135                 140

Glu Arg Phe Asn Arg Trp Phe Leu Thr Gly Met Thr Val Ala Gly Val
145                 150                 155                 160

Val Leu Leu Gly Ser Leu Phe Ser Arg Lys
                165                 170
```